(12) United States Patent
Smetona et al.

(10) Patent No.: US 10,245,338 B2
(45) Date of Patent: Apr. 2, 2019

(54) ULTRAVIOLET DIFFUSIVE ILLUMINATION

(71) Applicant: Sensor Electronic Technology, Inc., Columbia, SC (US)

(72) Inventors: Saulius Smetona, Concord, NC (US); Alexander Dobrinsky, Loudonville, NY (US); Yuri Bilenko, Columbia, SC (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/387,583

(22) Filed: Dec. 21, 2016

(65) Prior Publication Data

US 2017/0095585 A1   Apr. 6, 2017

Related U.S. Application Data

(63) Continuation of application No. 14/478,266, filed on Sep. 5, 2014, now Pat. No. 9,550,004.

(60) Provisional application No. 61/874,975, filed on Sep. 6, 2013, provisional application No. 61/911,155, filed on Dec. 3, 2013.

(51) Int. Cl.
*A61L 2/10* (2006.01)
*H05B 33/08* (2006.01)
*H05B 37/02* (2006.01)

(52) U.S. Cl.
CPC ............ *A61L 2/10* (2013.01); *H05B 33/0854* (2013.01); *H05B 37/0227* (2013.01); *A61L 2202/14* (2013.01)

(58) Field of Classification Search
CPC .......... A61L 2/08; A61L 2/10; A61L 2202/14; H05B 37/0227; H05B 33/0854
See application file for complete search history.

(56) References Cited

U.S. PATENT DOCUMENTS

| 4,933,602 A | * | 6/1990 | Ono | H01J 65/04 313/231.01 |
| 5,446,289 A | | 8/1995 | Shodeen et al. | |
| 6,669,838 B1 | * | 12/2003 | Baarman | A61L 2/10 210/103 |

(Continued)

FOREIGN PATENT DOCUMENTS

CN    101743431 A    6/2010
CN    101978210 A    2/2011

(Continued)

OTHER PUBLICATIONS

UV Sterilizer for iPhone, printed from http://www.sinco-elec.com/e_products/Portable-UV-Sterilizer-for-iPhoneiPod-p126.html on Dec. 17, 2013, 2 pages.

(Continued)

*Primary Examiner* — David E Smith
(74) *Attorney, Agent, or Firm* — LaBatt, LLC

(57) ABSTRACT

A solution for generating ultraviolet diffusive radiation is provided. A diffusive ultraviolet radiation illuminator includes at least one ultraviolet radiation source located within a reflective cavity that includes a plurality of surfaces. At least one of the plurality of surfaces can be configured to diffusively reflect at least 70% of the ultraviolet radiation and at least one of the plurality of surfaces can be configured to transmit at least 30% of the ultraviolet radiation and reflect at least 10% of the ultraviolet radiation.

20 Claims, 27 Drawing Sheets

(56) References Cited

U.S. PATENT DOCUMENTS

| | | | |
|---|---|---|---|
| 6,863,428 B2 | 3/2005 | Lundin | |
| 9,550,004 B2 | 1/2017 | Smetona et al. | |
| 2003/0150475 A1 | 8/2003 | Abrams et al. | |
| 2004/0166018 A1* | 8/2004 | Clark | A61L 9/205 422/4 |
| 2005/0143793 A1 | 6/2005 | Korman et al. | |
| 2006/0207431 A1* | 9/2006 | Baca | A61L 2/0011 96/224 |
| 2006/0255291 A1 | 11/2006 | Harris | |
| 2007/0047228 A1* | 3/2007 | Thompson | G02B 6/0018 362/237 |
| 2007/0075268 A1 | 4/2007 | Harris | |
| 2008/0074901 A1 | 3/2008 | David et al. | |
| 2008/0150475 A1 | 6/2008 | Kato et al. | |
| 2008/0225270 A1* | 9/2008 | Senga | G01N 21/64 356/51 |
| 2008/0265179 A1 | 10/2008 | Havens et al. | |
| 2009/0244903 A1* | 10/2009 | Wong | F21V 7/09 362/308 |
| 2009/0280035 A1* | 11/2009 | Koudymov | A23L 3/28 422/108 |
| 2010/0002414 A1 | 1/2010 | Meir et al. | |
| 2010/0165621 A1 | 7/2010 | Hoffend, Jr. et al. | |
| 2010/0177535 A1* | 7/2010 | Sato | G02F 1/133605 362/606 |
| 2011/0018012 A1 | 1/2011 | Tanaka et al. | |
| 2011/0198509 A1* | 8/2011 | Gostein | G01J 1/02 250/372 |
| 2012/0039076 A1 | 2/2012 | Chuang | |
| 2012/0128890 A1 | 5/2012 | Mirchev | |
| 2012/0261593 A1* | 10/2012 | Noori | A61L 2/10 250/492.1 |
| 2013/0078142 A1 | 3/2013 | Gordon | |
| 2014/0083482 A1 | 3/2014 | Hebrink | |
| 2014/0186500 A1* | 7/2014 | Lu | A23L 3/28 426/248 |
| 2014/0341777 A1* | 11/2014 | Deshays | A61L 2/24 422/24 |

FOREIGN PATENT DOCUMENTS

| | | | |
|---|---|---|---|
| DE | 60026458 T2 | 9/2006 | |
| KR | 200425562 Y1 | 9/2006 | |
| KR | 100838348 B1 | 6/2008 | |
| WO | 2005114265 A1 | 12/2005 | |
| WO | WO 2005114265 A1 * | 12/2005 | G02B 5/02 |
| WO | WO 2013096243 A1 * | 6/2013 | G01N 21/6486 |

OTHER PUBLICATIONS

GORE® Diffuse Reflector Product, printed from http://www.gore.com/en_xx/products/electronic/specialty/specialty.html?RDCT=gore.com on Sep. 5, 2014, 2 pages.

Smith, D., U.S. Appl. No. 14/478,266, Notice of Allowance, dated Aug. 26, 2016, 10 pages.

Smith, D., U.S. Appl. No. 14/478,266, Final Office Action 1, dated Mar. 16, 2016, 22 pages.

Smith, D., U.S. Appl. No. 14/478,266, Non-Final Office Action 1, dated Sep. 3, 2015, 30 pages.

Pan, Chinese Application No. 201480048772.0, Office Action1—English translation, dated Sep. 29, 2016, 18 pages.

Kim, International Application No. PCT/US2014/054240, International Search Report and Written Opinion, dated Dec. 22, 2014, 13 pages.

Pan, Chinese Application No. 201480048772.0, Office Action2 with English translation, dated Jul. 4, 2017, 22 pages.

Pan, Chinese Application No. 201480048772.0, Rejection Decision, dated Jan. 31, 2018, 12 pages German Application No. 11 2014 004 109.2, Machine translation of pp. 5-8 of Office Action1, dated Oct. 27, 2017, 4 pages.

Chinese patent office, Application No. 201480048772.0, Notice of Allowance, Oct. 24, 2018, 2 pages. (English Translation not available).

Smith, D., U.S. Appl. No. 15/852,988, Office Action 1, Dec. 18, 2018, 18 pages.

* cited by examiner

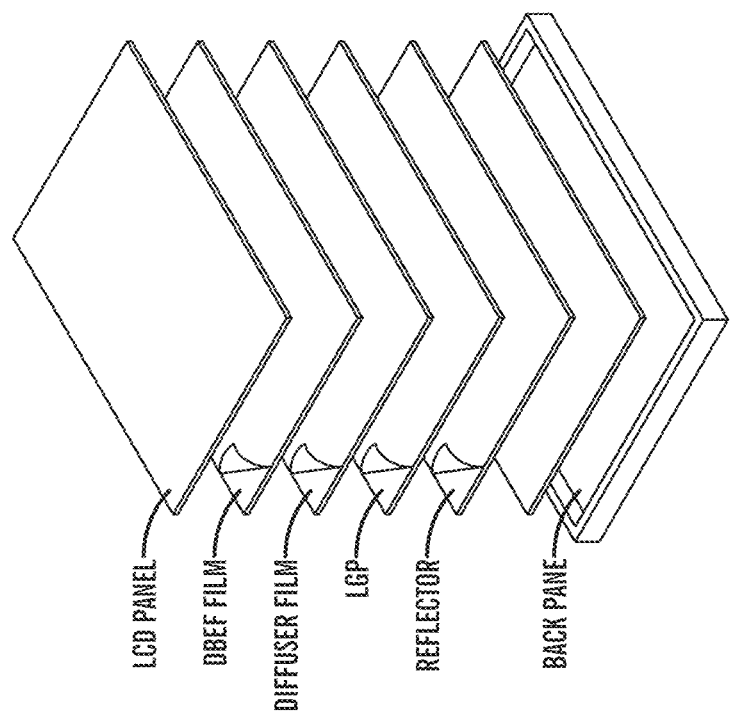
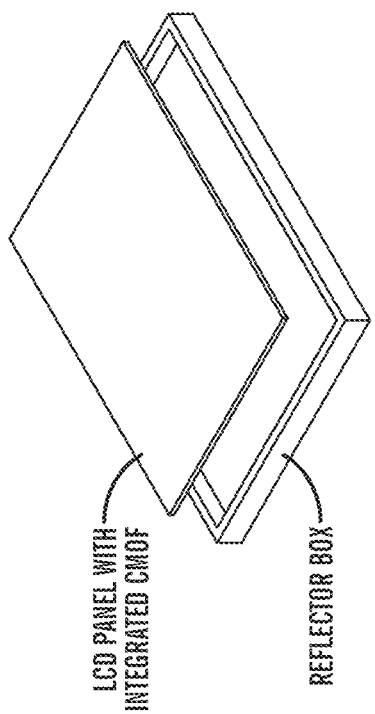
FIG. 1A
*PRIOR ART*
FIG. 1B
*PRIOR ART*

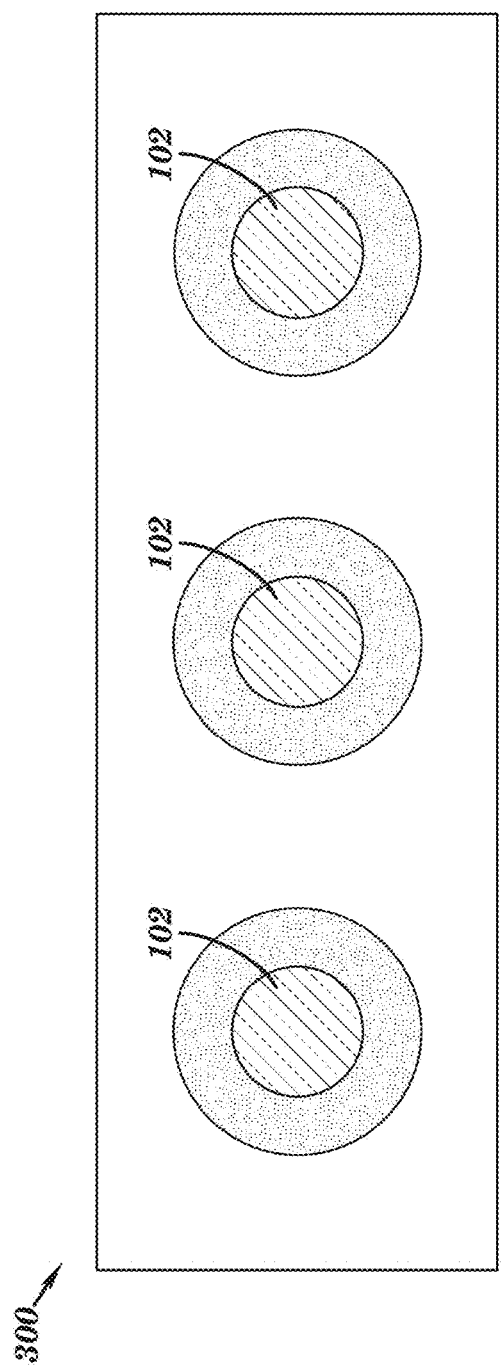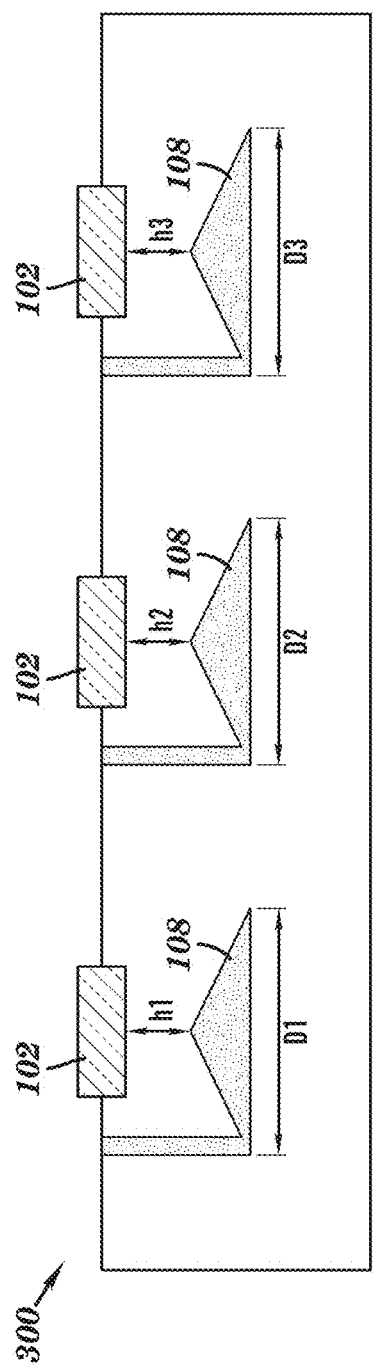

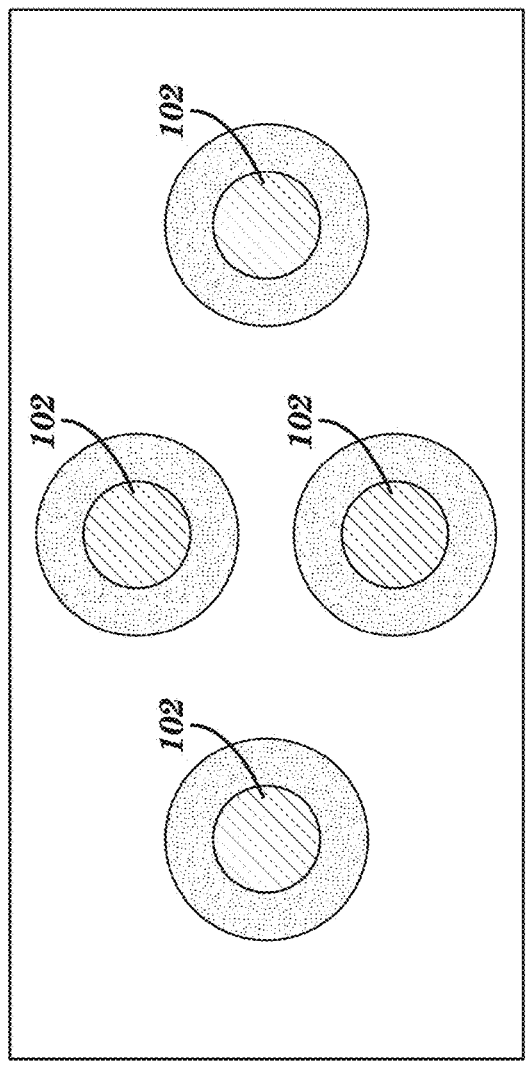
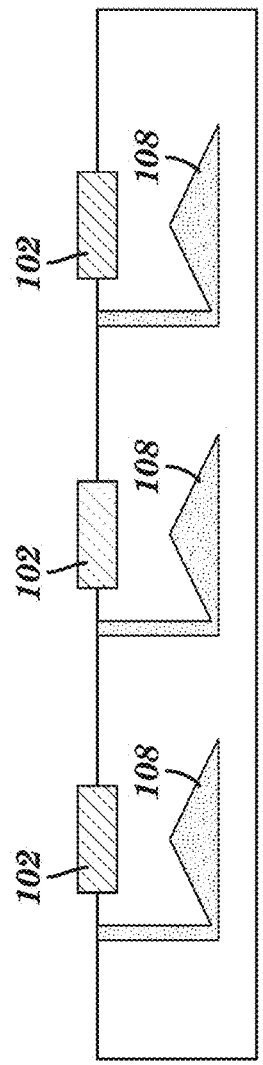
FIG. 10A
FIG. 10B

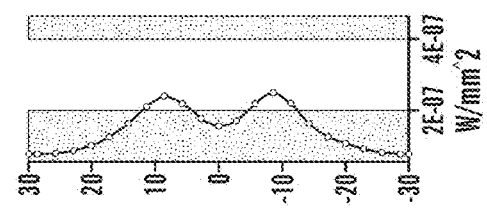
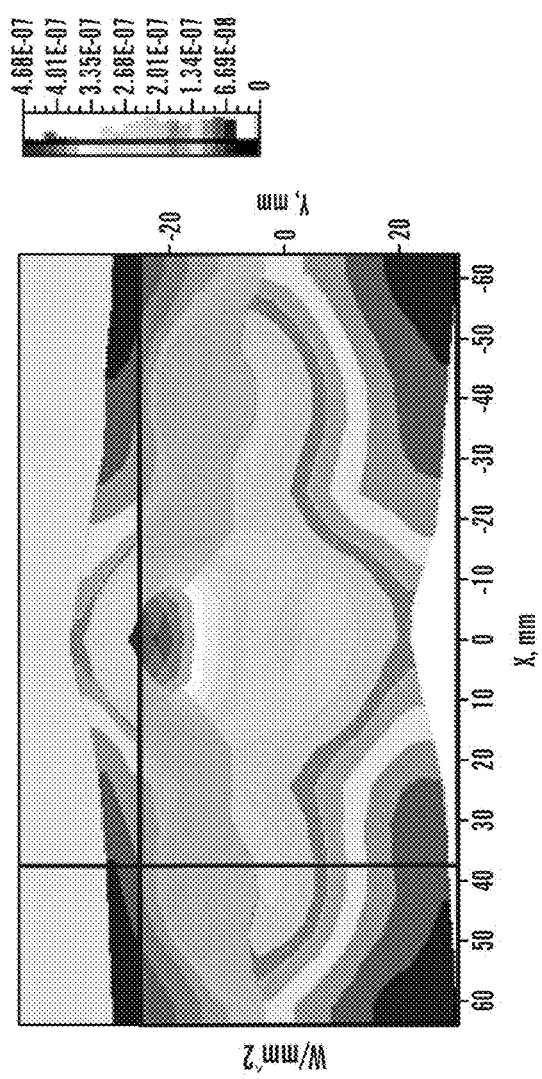
FIG. 11A
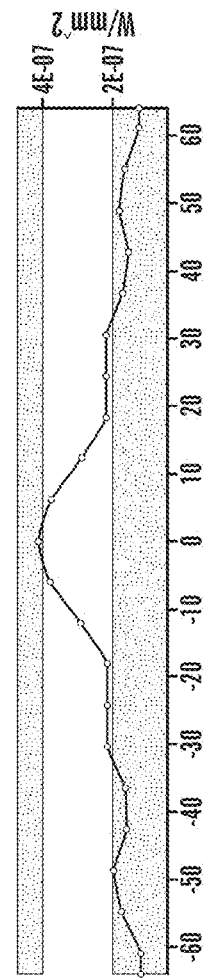
FIG. 11B
FIG. 11C

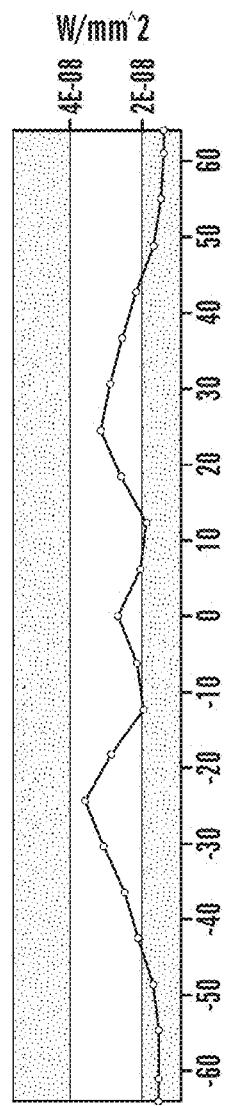
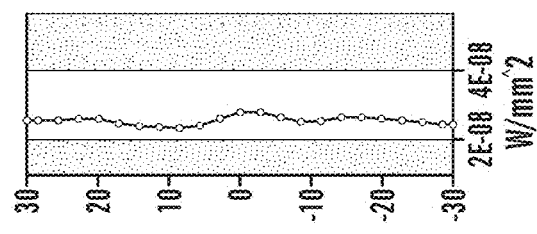
FIG. 12D
FIG. 12C

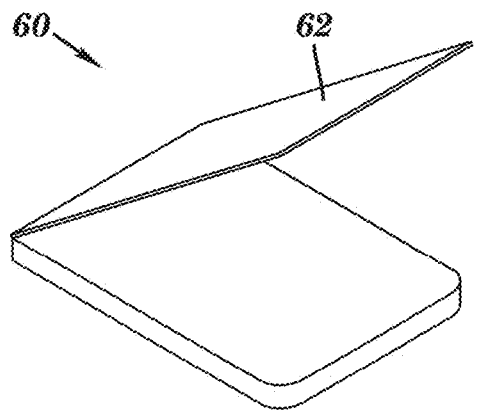
FIG. 24
 
FIG. 25A     FIG. 25B

ULTRAVIOLET DIFFUSIVE ILLUMINATION

REFERENCE TO RELATED APPLICATIONS

The current application is a continuation of U.S. patent application Ser. No. 14/478,266, which was filed on 5 Sep. 2014, and which claims the benefit of U.S. Provisional Application No. 61/874,975, which was filed on 6 Sep. 2013, and U.S. Provisional Application No. 61/911,155, which was filed on 3 Dec. 2013, each of which is hereby incorporated by reference.

TECHNICAL FIELD

The disclosure relates generally to ultraviolet radiation, and more particularly, to a solution for generating diffusive ultraviolet radiation.

BACKGROUND ART

The use of light diffusers is common in backlight illumination, which is frequently found in liquid crystal displays (LCDs). For visible light, the criterion of diffuser design is significantly different than that for ultraviolet (UV) radiation. This is largely related to the fact that UV transparent materials are harder to manufacture than corresponding materials for visible light. Further, the transparency of UV materials is typically inferior to the transparency of materials to visible light. In addition, the UV transparent materials are expensive compared to materials transparent to visible light.

Recently, various improvements to backlight visible light illumination design have been proposed. For example, collimating multi-layer optical film (CMOF) provides a cost efficient light management for LCD backlights with integrated optical films. These films provide diffusive capability to LCD backlight illuminators. CMOF is based on multi-layer optical film technology that is used to make current display films, such as dual brightness enhancement film (DBEF), reflective polarizers, and enhanced specular reflector (ESR) films. The CMOFs are used in a new backlight architecture developed by 3M™ and branded as Air Guide. CMOF technology combines two types of nanotechnologies: nanolayer optics and ultra-low refractive index nanofoam. The CMOF film is attached directly to the LCD panel, replacing several separate films used in current light emitting diode (LED) backlight designs. The new design uses a hollow cavity with no free-floating films and no solid light guide. In the Air Guide design, light is spread through the air of the cavity between the LCD panel and the highly reflective film. FIGS. 1A and 1B illustrate the schematics of a previous LED backlight design and 3M's Air Guide design, respectively.

Another traditional design for diffusive wave guiding is shown in FIGS. 2A and 2B. In this design, the LED lights are positioned at a side of the diffuser (see FIG. 2B, for example). The diffuser is composed of several layers: a sheet with micro-features, reflecting and light guiding sheets, and a diffusive sheet followed by optional prismatic and other diffusive sheets. For success of such a design, good light reflective and light transparent materials have to be employed, which is difficult to achieve for ultraviolet illumination.

Currently, UV devices capable of operating to sterilize mobile phones are available, such as the UV Sterilizer for iPhone from Sinco-Elec. Co. This UV sterilizer is a desktop unit that allows a user to place a mobile phone into the sterilizer for about five minutes for UV sterilization. The device turns a blue LED on to indicate the sterilization is in process. Completion of the sterilization process is indicated by the blue indicator LED turning off. The device does not utilize low voltage light emitting diodes and cannot be used as a carry-case.

SUMMARY OF THE INVENTION

In view of the prior art, the inventors have identified various challenges and limitations of current approaches for generating systems that use ultraviolet (UV) radiation. For example, the inventors have noted that current approaches are unable to use diffusive UV illumination. Such an inability can be caused by, for example, a difficulty in implementing good light reflective and light transparent materials in conjunction with an effective diffusive UV illumination design.

The present invention proposes a diffusive illuminator that can effectively employ air, a high performance polymer, and/or the like, which are transparent to ultraviolet light within a reflective enclosure. In an embodiment, the diffusive illuminator can be implemented in a system for disinfecting an object.

Aspects of the invention provide a solution for generating diffusive ultraviolet radiation. A diffusive ultraviolet radiation illuminator includes at least one ultraviolet radiation source located within a reflective cavity that includes a plurality of surfaces. At least one of the plurality of surfaces can be configured to diffusively reflect at least 70% of the ultraviolet radiation and at least one of the plurality of surfaces can be configured to transmit at least 30% of the ultraviolet radiation and reflect at least 10% of the ultraviolet radiation.

A first aspect of the invention provides an illuminator comprising: at least one ultraviolet radiation source configured to generate ultraviolet radiation; and a reflective cavity comprising a plurality of surfaces, wherein the at least one ultraviolet radiation source is located within the reflective cavity, and wherein at least one of the plurality of surfaces is configured to diffusively reflect at least 70% of the ultraviolet radiation, and at least one of the plurality of surfaces is configured to transmit at least 30% of the ultraviolet radiation and reflect at least 10% of the ultraviolet radiation.

A second aspect of the invention provides system comprising: an enclosure configured to contain an object for disinfection; and an illuminator located within the enclosure, the illuminator comprising at least one ultraviolet radiation source configured to generate ultraviolet radiation; and a reflective cavity comprising a plurality of surfaces, wherein the at least one ultraviolet radiation source is located within the reflective cavity, and wherein at least one of the plurality of surfaces is configured to diffusively reflect at least 70% of the ultraviolet radiation, and at least one of the plurality of surfaces is configured to transmit at least 30% of the ultraviolet radiation and reflect at least 10% of the ultraviolet radiation.

A third aspect of the invention provides an illuminator comprising: at least one ultraviolet radiation source configured to generate ultraviolet radiation; and a reflective cavity comprising a plurality of surfaces, wherein the at least one ultraviolet radiation source is located within the reflective cavity, and wherein at least one of the plurality of surfaces is configured to diffusively reflect at least 70% of the ultraviolet radiation, and the diffusively reflected ultraviolet radiation is less than approximately 10% different from a diffusive Lambertian reflectivity for an angle of reflectance.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 1A and 1B illustrate the schematics of a previous LED backlight design and 3M's Air Guide design, respectively.

FIGS. 7A and 7B show a top view and a cross-sectional view, respectively, of an illustrative illuminator according to an embodiment.

FIGS. 10A and 10B show a top view and a cross-sectional view, respectively, of an illustrative illuminator according to an embodiment.

FIGS. 11A-11C show an intensity distribution for the illustrative illuminator shown in FIGS. 10A and 10B.

FIG. 12A shows an illustrative reflecting mirror according to an embodiment, while FIGS. 12B-12D show an intensity distribution for an illuminator including the illustrative reflecting mirror in FIG. 12A.

FIG. 24 shows a device including a diffusive illuminator for disinfecting electronic gadgets according to an embodiment.

FIGS. 25A and 25B show the effect of ultraviolet radiation on *E. coli* colonies.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2A:
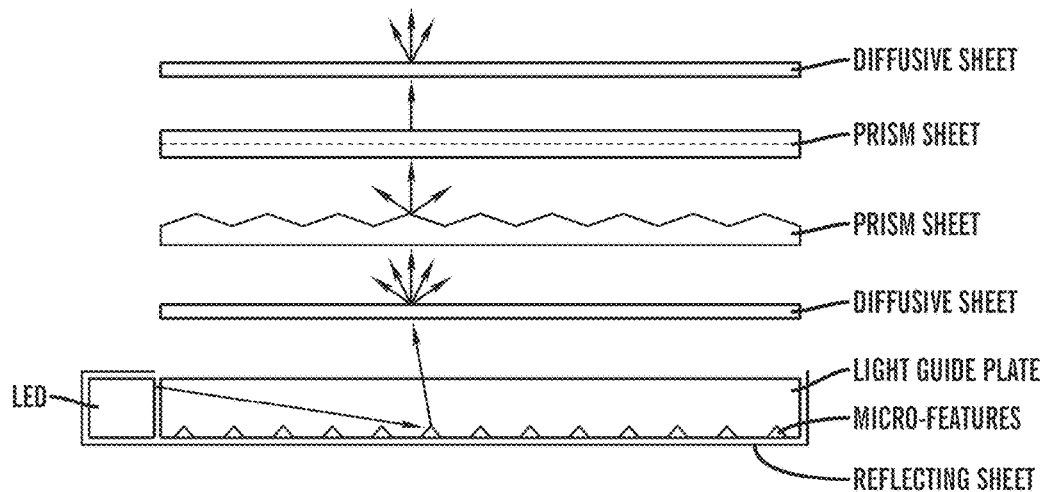
FIGS. 2A and 2B show a diffusive wave guiding design according to the prior art.
Figure 2B:
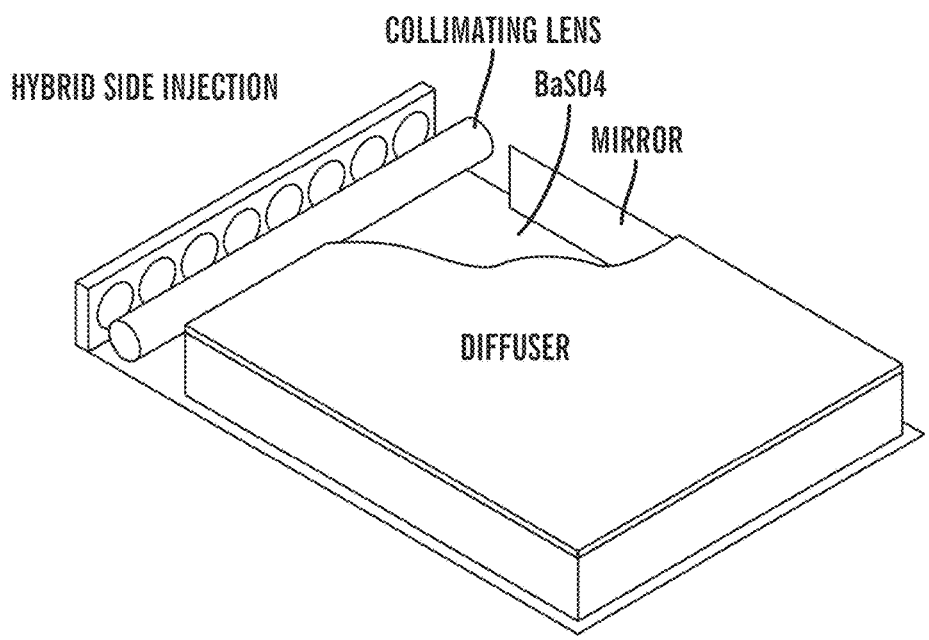

As indicated above, aspects of the invention provide a solution for diffusively reflecting ultraviolet radiation, e.g., for disinfection purposes. A diffusive ultraviolet radiation illuminator can include at least one ultraviolet radiation source located within a reflective cavity. The reflective cavity includes a plurality of surfaces, at least one of which can be configured to diffusively reflect at least 70% of the ultraviolet radiation and at least one of the plurality of surfaces can be configured to transmit at least 30% of the ultraviolet radiation and reflect at least 10% of the ultraviolet radiation.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows at least ten percent of the ultraviolet light, which is radiated at a normal incidence to an interface of the layer, to pass there through.

As used herein, the term "disinfection" and its related terms means treating a product, device, food item, and/or the like, hereinafter "the item," so that it includes a sufficiently low number of contaminants (e.g., chemical) and microorganisms (e.g., virus, bacteria, and/or the like) and can be handled as part of a desired human interaction with no or no reasonable risk for the transmission of a disease or other harm to the human. For example, disinfection of the item means that the item has a sufficiently low level of active microorganisms and/or concentration of other contaminants that a typical human can interact with the item without suffering adverse effects from the microorganisms and/or contaminants present on the item. In addition, disinfection can include sterilization. As used herein, the term "sterilization" and its related terms means neutralizing an ability of a microorganism to reproduce, which may be accomplished without physically destroying the microorganism. In this example, a level of microorganisms present on the item cannot increase to a dangerous level and will eventually be reduced, since the replication ability has been neutralized. A target level of microorganisms and/or contaminants can be defined, for example, by a standards setting organization, such as a governmental organization.

Figure 3:
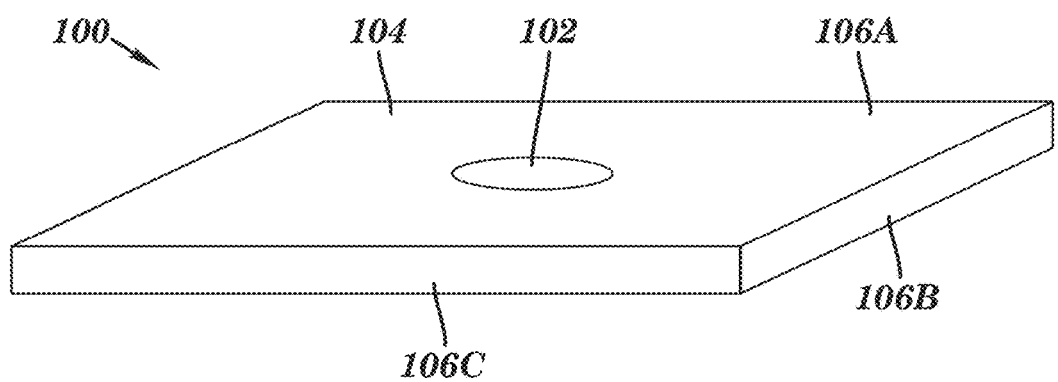
FIG. 3 shows an illustrative illuminator according to an embodiment.

Turning to the drawings, FIG. 3 shows an illustrative illuminator 100 for providing diffusive ultraviolet radiation according to an embodiment. The illuminator 100 can be used, for example, to disinfect any item, such as an electronic device (e.g., a mobile phone, a tablet, a music player, a laptop, a computer keyboard, and/or the like), a food item, a storage container used for food preservation, disinfection, sterilization, chemical modification, and/or the like, any type of item used at a medical facility (e.g., hospital bed, hospital sheets, pillows, and/or the like), and/or the like.

As shown, the illuminator 100 can include at least one ultraviolet radiation source 102. The ultraviolet radiation source 102 can comprise any combination of one or more ultraviolet radiation emitters. For example, the ultraviolet radiation source 102 can include a high intensity ultraviolet lamp (e.g., a high intensity mercury lamp), a discharge lamp, an ultraviolet light emitting diode (LED), super luminescent LEDs, laser diodes, and/or the like. In an embodiment, the ultraviolet radiation source 102 includes a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the ultraviolet radiation source 102 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, within a reflective cavity the illuminator 100. Illustrative wave guiding structures include, but are not limited to, a plurality of ultraviolet fibers, each of which terminates at an opening, a diffuser, and/or the like.

As discussed herein, the illuminator 100 can include a reflective cavity 104 into which the at least one ultraviolet radiation source 102 directs the generated ultraviolet radiation. The reflective cavity 104 can be a rectangular cuboid shape that includes a top surface 106A, side surfaces 106B, and a bottom surface 106C. However, it is understood that the rectangular cuboid is only illustrative, and that the reflective cavity 104 can comprise a polyhedron having any shape, such as a cube, a pyramid, and/or the like, and can have rounded edges/corners, comprise a sphere, and/or the like. The dimensions (e.g., length, width, height, volume, and/or the like) of the reflective cavity 104 can be designed according to the application (e.g., disinfection). For example, for applications designed to disinfect a particular item or type of item, the dimensions can be customized based on the known dimensions of the item. In an embodiment, the illuminator 100 can be used to disinfect smaller electronic gadgets, in which case the reflective cavity 104 of the illuminator 100 can be on the order of a few centimeters or a few tens of centimeters.

In an embodiment, at least some of the surfaces of the reflective cavity 104 are highly reflective and are capable of reflecting at least 70% of the ultraviolet radiation incident to the surface(s). In an embodiment, at least 50% of the surfaces of the reflective cavity 104 are highly reflective. In a more specific embodiment, at least a top surface 106A is capable of reflecting at least 70% of the ultraviolet radiation. The measure of reflective efficiency for the illuminator 100 is related to the total reflected incident energy that is being reflected. The measure includes reflectivity of light incoming at any angle and reflected at multiple angles (e.g., diffusively reflected). It is understood that the reflectivity of each surface within the reflective cavity 104 may not be the same. For example, the side walls 106B can be specularly reflective, while the top surface 105A can be diffusively reflective or a combination of diffusively and specularly reflective. Each surface may be also made of a different reflective material and/or covered in a different reflective film coating. For example, the side surfaces 106B can include a material such as a highly polished aluminum, and/or the like, while the top surface 106A or a portion thereof can include a diffusively reflective material, such as a highly ultraviolet reflective expanded polytetrafluoroethylene (ePTFE) membrane (e.g., GORE® Diffuse Reflector Material), and/or the like.

One or more of the surfaces in the reflective cavity 104 can diffusively reflect the ultraviolet radiation according to a Lambertian distribution. In this embodiment, the intensity of the reflected light is directly proportional to the cos (A), where A is the angle between the surface normal and the direction of reflected light. In an embodiment, the diffusive ultraviolet radiation from the illuminator 100 is at most 10% different from a uniform Lambertian distribution of diffusive reflectivity for an angle of reflectance. Such a difference can be calculated, for example, as a difference from Lambert's cosine law, which states that a reflected radiation at an angle A to a surface is given by the formula $I_0 \times \cos(A)$, where $I_0$ is the intensity measured at a location normal to the surface. In this case, a difference of 10% or less from the uniform Lambertian distribution means that the actual reflected radiation at any angle A to the surface is within +/−10% of $I_0 \times \cos(A)$.

At least one of the surfaces of the reflective cavity 104 can be configured to be partially transmitting and partially reflective. For example, the bottom surface 106C, as an exit surface for the diffusive ultraviolet radiation, can include a material that is partially transmitting, and partially reflective. In an embodiment, the bottom surface 106C can be at least 30% transmitting and at least 10% reflective. In a more specific embodiment, the partially transmitting and partially reflective surface is at least 60% transmitting and more than 30% reflective. It is understood that transmission in the range of 30-70% is acceptable, while reflectivity is in the range of 65-25%, or higher. The partially transmitting and partially reflective surface of the reflective cavity 104 can provide an exit surface for the diffusive ultraviolet radiation. In an embodiment, the bottom surface 106C can include a partially transparent film that is made of a UV transparent material, such as fused silica, Teflon, and/or the like. In a more specific embodiment, the partially transparent film can include a roughness, a patterning, or a means for vibrating to improve the diffusive reflectivity. It is understood that the film can contain small absorption losses. In an embodiment, the partially transparent film has less than 10% absorption losses. Furthermore, the partially transparent film can also be diffusively reflective.

Figure 4A:
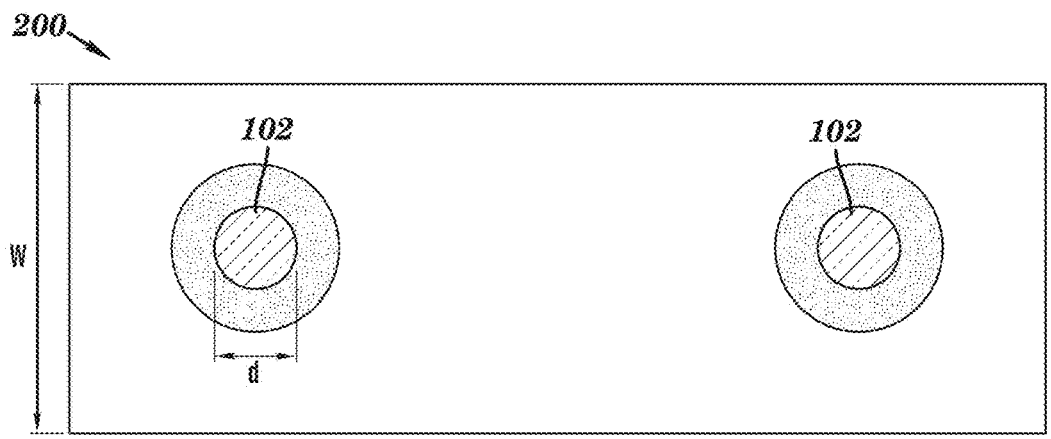
FIGS. 4A and 4B show a top view and a cross-sectional view, respectively, of an illustrative illuminator according to an embodiment.
Figure 4B:
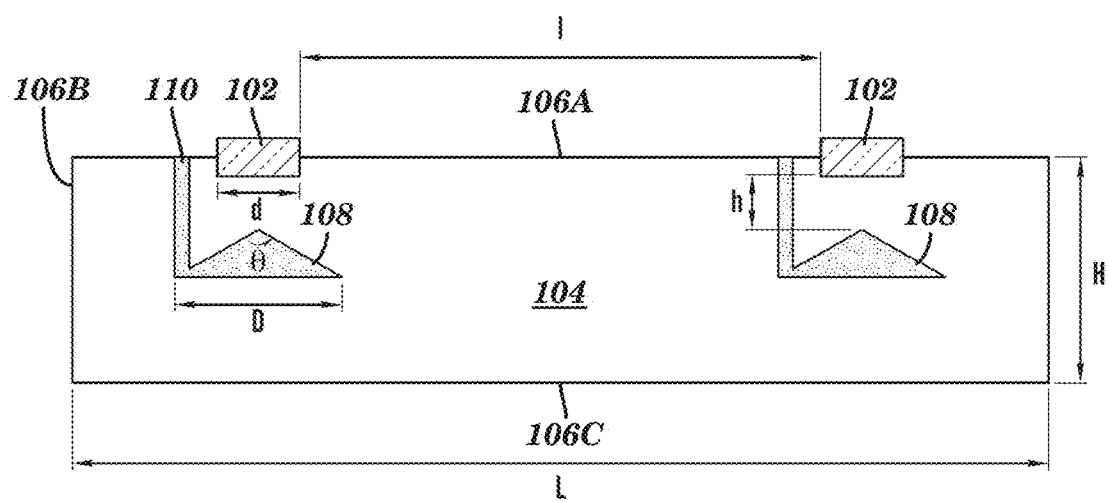

It is understood that an illuminator can include any number of ultraviolet radiation sources. Turning now to FIGS. 4A and 4B, an illustrative illuminator 200 according to an embodiment is shown. In this embodiment, the illuminator 200 includes two ultraviolet radiation sources 102, which can be positioned on a surface in the reflective cavity 104 that is highly reflective. For example, in FIGS. 4A and 4B, the ultraviolet radiation sources 102 are positioned on a highly reflective surface of the reflective cavity 104 (e.g., the top surface 106A). The ultraviolet radiation sources 102 can be positioned along a centerline of the reflective cavity 104. The spacing "I" between the ultraviolet radiation sources 102 can depend upon the overall length "L" of the reflective cavity 104, but also can be designed to uniformly distribute the intensity of the ultraviolet radiation generated by the ultraviolet radiation sources 102 throughout the cavity 104.

The illuminator 200 can include a set of reflecting mirrors 108, each of which is located directly beneath an ultraviolet radiation source 102. The reflecting mirrors 108 can comprise a highly diffusive ultraviolet radiation material, such as a highly ultraviolet reflective expanded polytetrafluoroethylene (ePTFE) membrane (e.g., GORE® Diffuse Reflector Product (DRP)), and/or the like. In an embodiment, the reflecting mirrors 108 can comprise a fluoropolymer, such as fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), Teflon, and/or the like. In still another embodiment, the reflecting mirrors 108 can be partially UV reflecting, partially UV transparent. For example, the reflecting mirrors 108 can comprise an UV reflective film over an UV transparent film. In an embodiment, the reflecting mirrors 108 can be configured to provide specular reflection and can comprise, for example, polished aluminum, and/or the like.

The reflecting mirrors 108 can be configured to both diffusively reflect and recirculate the ultraviolet radiation. For example, the reflecting mirrors 108 can form a cone shape with a vertex that is directed towards the ultraviolet radiation source 102. The vertex of the reflecting mirror 108 is located a distance "h" from the ultraviolet radiation source 102. The distance "h" is typically on the order of the diameter "d" of the ultraviolet radiation source 102. In a specific embodiment, the distance "h" is a few millimeters, which is about ⅓ of the height "H" of the cavity 104. The diameter "d" for the ultraviolet radiation source 102 can be smaller than the diameter "D" of the reflecting mirror 108. In an embodiment, the half angle θ/2 of the reflecting mirror 108 (e.g., the angle measured between a line drawn normal to the base of the cone and passing through the vertex of the cone and a line tangent to the surface of the cone and also passing through the vertex of the cone) is between approximately 20 degrees and approximately 80 degrees. The diameter D of the cone (e.g., reflecting mirror 108) can be calculated as $2h_1 \tan(\theta/2)$, where $h_1$ is the height of the cone and is comparable to the height h between the reflecting mirror 108 and the ultraviolet radiation source 102. In an embodiment, the diameter "D" of the reflecting mirror 108 is at least 5% of the width "W" of the reflective cavity 104. The reflecting mirrors 108 can be highly reflective and have at least 70% reflectivity. The reflecting mirrors 108 can include a vertex angle, θ, which is at least 40 degrees. In a more specific embodiment, the vertex angle θ is at least 90 degrees.

Figure 5:
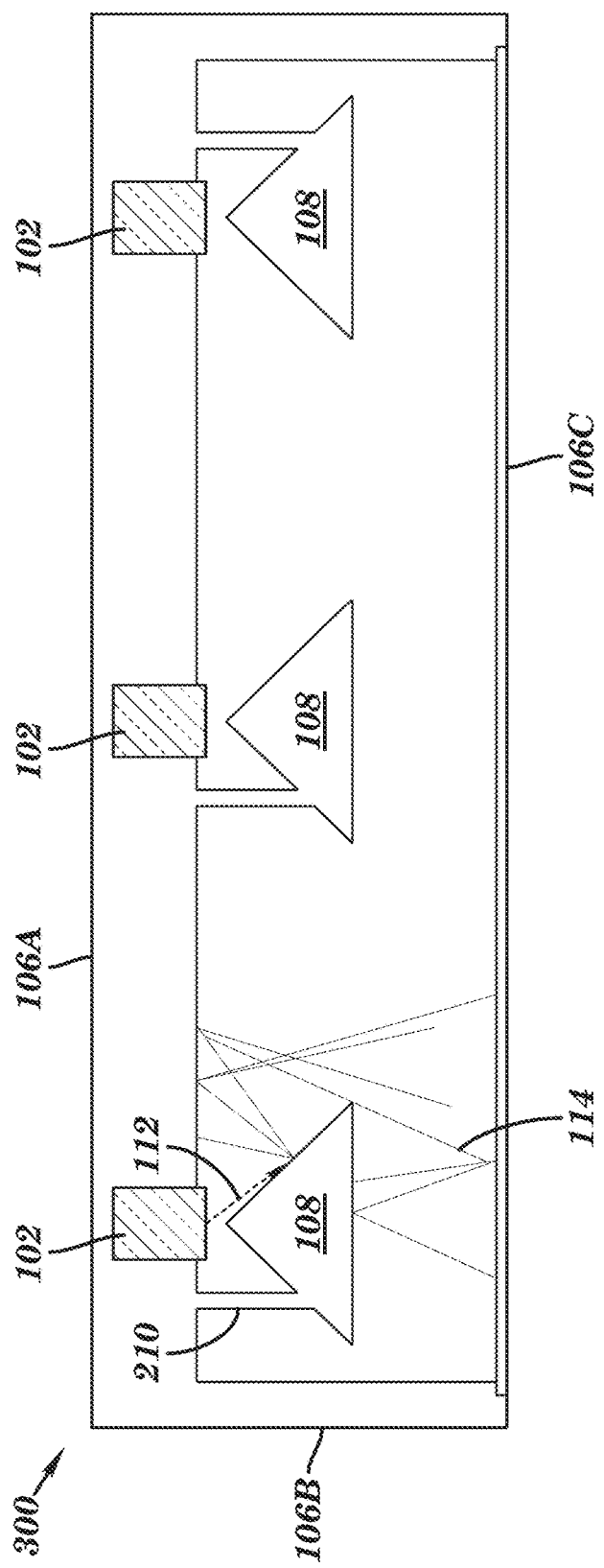
FIG. 5 shows an illustrative illuminator according to an embodiment.

The reflecting mirrors 108 can be mounted within the reflective cavity 104 via at least one leg 110 that is attached to the reflective cavity 104. For example, in FIG. 4B, a leg 100 attaches each reflecting mirror 108 to the top surface 106A of the reflective cavity. The legs 110 can be attached to any portion of the reflecting mirror 108. In the embodiment of an illuminator 300 shown in FIG. 5, the reflecting mirrors 108 are attached via legs 210 to the top surface 106A of the reflective cavity 104. In operation, an original incident of ultraviolet radiation 112 from the ultraviolet radiation source 102 can be diffusively reflected by the reflecting mirror 108 and then again diffusively reflected by the surfaces (e.g., top surface 106A) of the reflective cavity 104. This diffusive UV radiation exits the reflective cavity 104 through the partially transparent, partially reflective surface (e.g., bottom surface 106C).

Figure 6A:
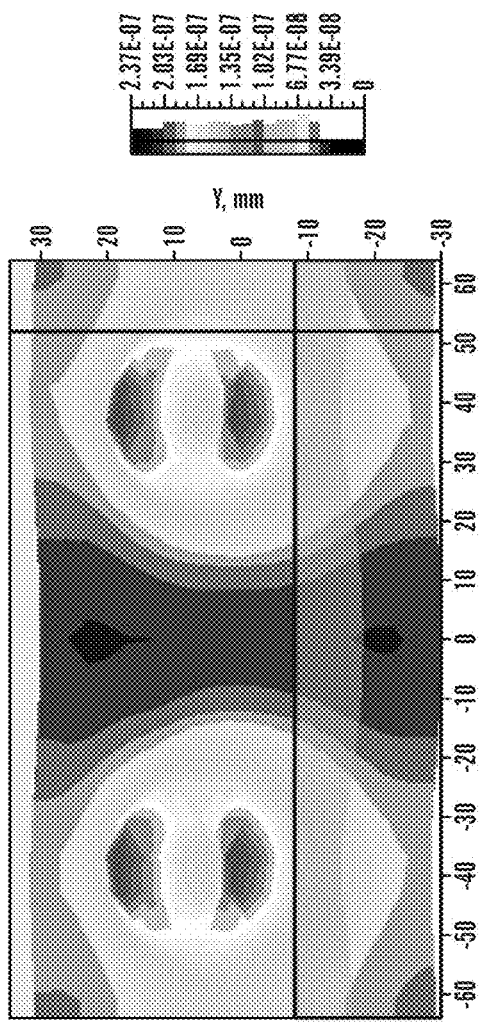
FIGS. 6A-6C show an intensity distribution for the illustrative illuminator shown in FIGS. 4A and 4B.
Figure 6C:
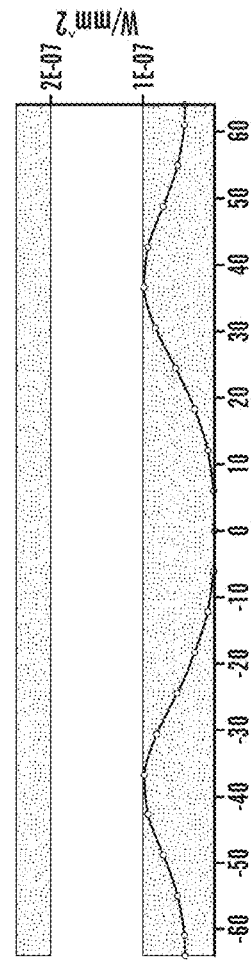
Figure 6B:
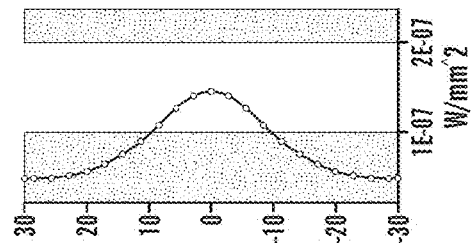

The reflecting mirrors 108 and the high diffusive reflectivity of the surfaces in the reflective cavity 104 distribute and diffusively reflect the ultraviolet radiation from the ultraviolet radiation sources 102 such that the bottom surface 106C of the illuminator 200 has an approximately Lambertian reflectance. FIGS. 6A-6C shows an intensity distribution for the illustrative illuminator shown in FIGS. 4A and 4B. As seen in the figures, the ultraviolet radiation sources 102 have a distinct peak at the location corresponding to the rim of the reflecting mirror 108. Directly below the ultraviolet radiation source 102, the intensity of the ultraviolet radiation is lower due to the reflecting mirror 108 shadowing. There is also a valley of intensity in an area between the ultraviolet radiation sources 102. The lowest value of the intensity within the valley is approximately ¼ of the peak intensity value. In a specific embodiment, the illuminator 200 is capable of generating radiative intensity of at least 1 micro watt per square centimeter in the regions of the lowest radiation intensity.

Figure 8B:
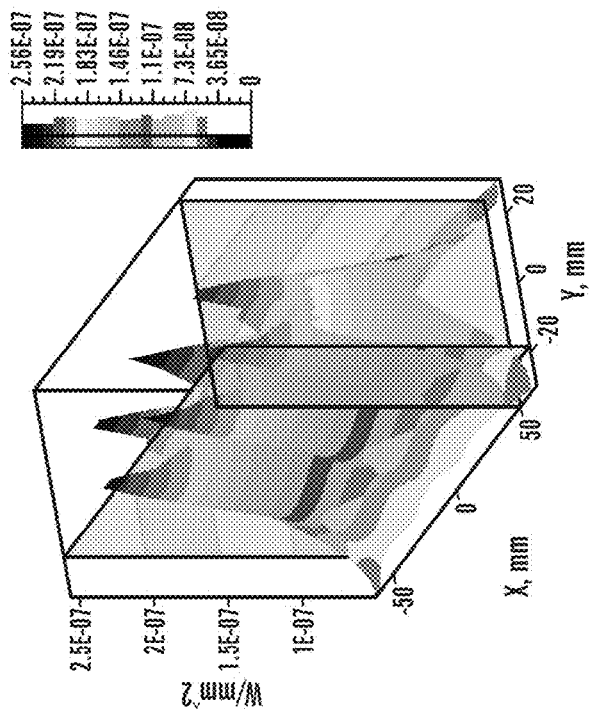
FIGS. 8A-8C show an intensity distribution for the illustrative illuminator shown in FIGS. 7A and 7B.
Figure 8A:
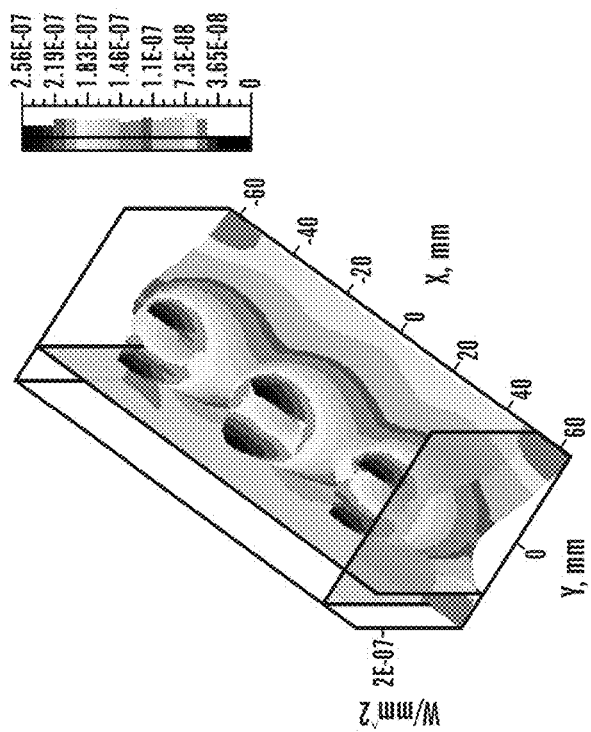
Figure 8C:
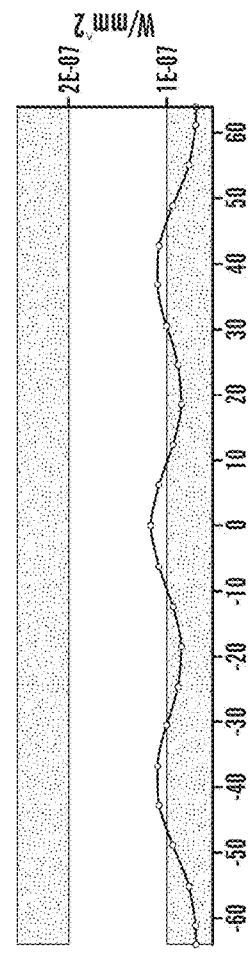
Figure 9:
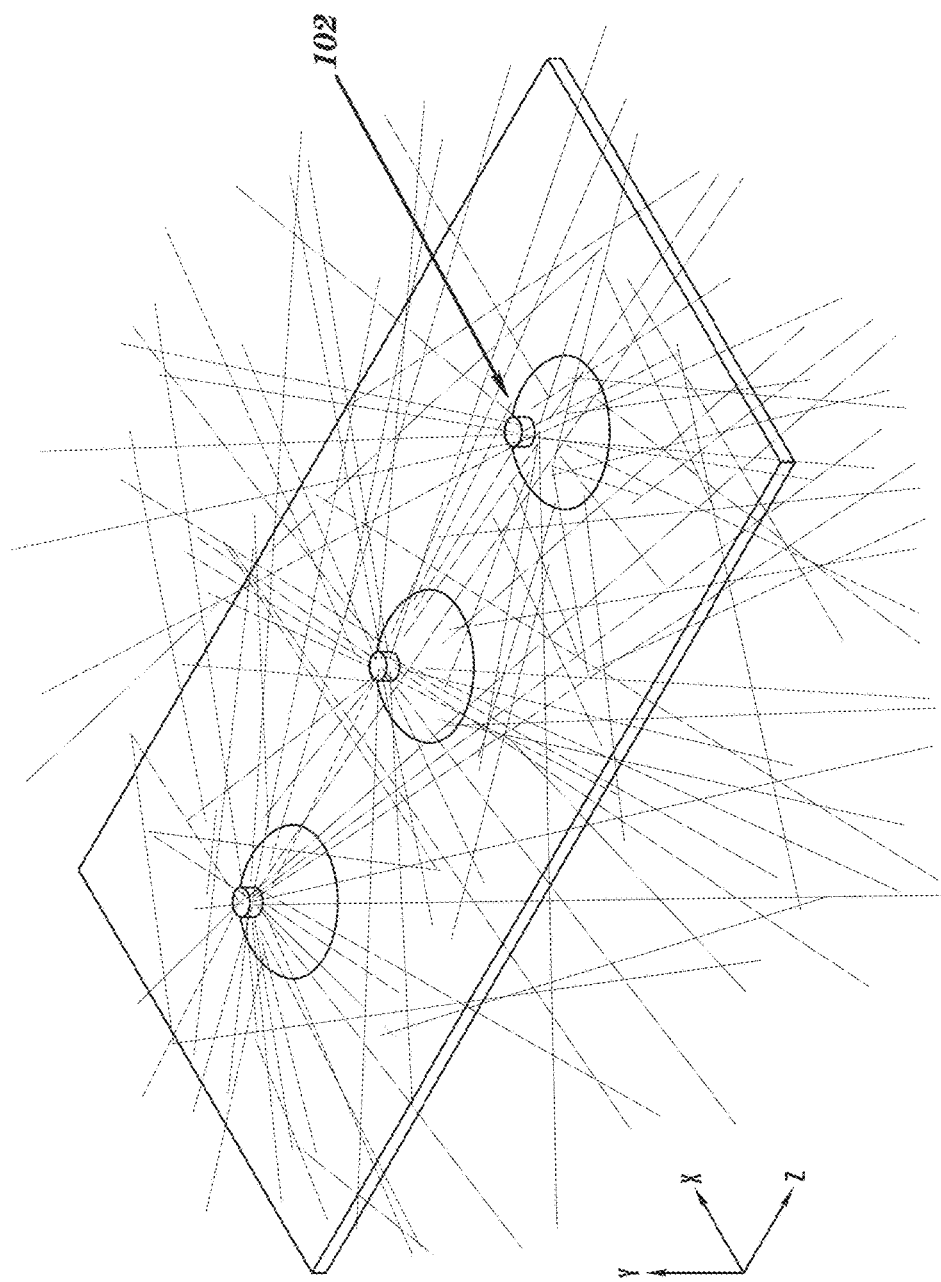
FIG. 9 shows a ray tracing simulation for the illustrative illuminator shown in FIGS. 7A and 7B.

Turning now to FIGS. 7A and 7B, an illustrative illuminator 300 according to another embodiment is shown. In this embodiment, there are three ultraviolet radiation sources 102, each with a reflecting mirror 108 below it. The distances h1, h2, h3 between the ultraviolet radiation source 102 and the corresponding reflecting mirror 108 can be the same, or the distances h1, h2, h3 can be different according to the desired distribution of ultraviolet radiation intensity throughout the reflective cavity. Additionally, the diameter D1, D2, D3 of each reflecting mirror 108 can also be the same or different. Adjusting the distances h1, h2, h3 and/or the diameters D1, D2, D3 adjusts the intensity of the ultraviolet radiation in the central region of the surface being illuminated. For example, reducing diameter D2 can increase the intensity of the ultraviolet radiation in the central region of the surface being illuminated. Increasing h2 can, for example, lead to a deeper shadow region directly beneath the reflecting mirror 108 including diameter D2 and increase the ultraviolet radiation illumination around the shadow region. In an embodiment, a simulation method, such as ray tracing and/or the like, can be used for simulating an illuminator with specific distances h1, h2, h3 and diameters D1, D2, D3, and for a given optical reflectivity, absorption, and transmission of the surfaces. The simulation can be used to optimize the distances h1, h2, h3 and/or diameters D1, D2, D3 while maintaining other attributes of the illuminator, such as the number and location of ultraviolet radiation sources 102, the dimensions of the illuminator, and/or the like. FIGS. 8A-8C illustrate the intensity distribution of the diffusive ultraviolet radiation at the exit surface (e.g., the bottom surface 106C) of the reflective cavity 104 for the illuminator 300 shown in FIGS. 7A and 7B. FIG. 9 illustrates a ray tracing simulation of the illuminator 300 including three ultraviolet radiation sources 102. In general, inclusion of a larger number of ultraviolet radiation sources 102, can provide a more uniform ultraviolet radiation distribution.

It is understood that an illuminator can include ultraviolet radiation sources in any type of arrangement. Turning to FIGS. 10A and 10B, an illustrative illuminator 400 is shown including four ultraviolet radiation sources 102 according to an embodiment. Similar to the embodiments shown in FIGS. 4A and 4B and FIGS. 7A and 7B, the illuminator 400 includes a reflecting mirror 108 directly beneath each ultraviolet radiation source 102. The intensity distribution of the diffusive ultraviolet radiation at the exit surface (e.g., the bottom surface 106C) of the reflective cavity 104 is illustrated in FIGS. 11A-11C. Comparing the intensity distribution shown in FIG. 8C and the intensity distribution shown in FIG. 11C, the addition of an ultraviolet radiation source and a modification to the spatial arrangement of the ultraviolet radiation sources results in a significant increase in the intensity of the ultraviolet radiation. For example, in FIG. 11C, the intensity at the center is significantly larger than the intensity at the center in FIG. 8C.

Figure 12A:
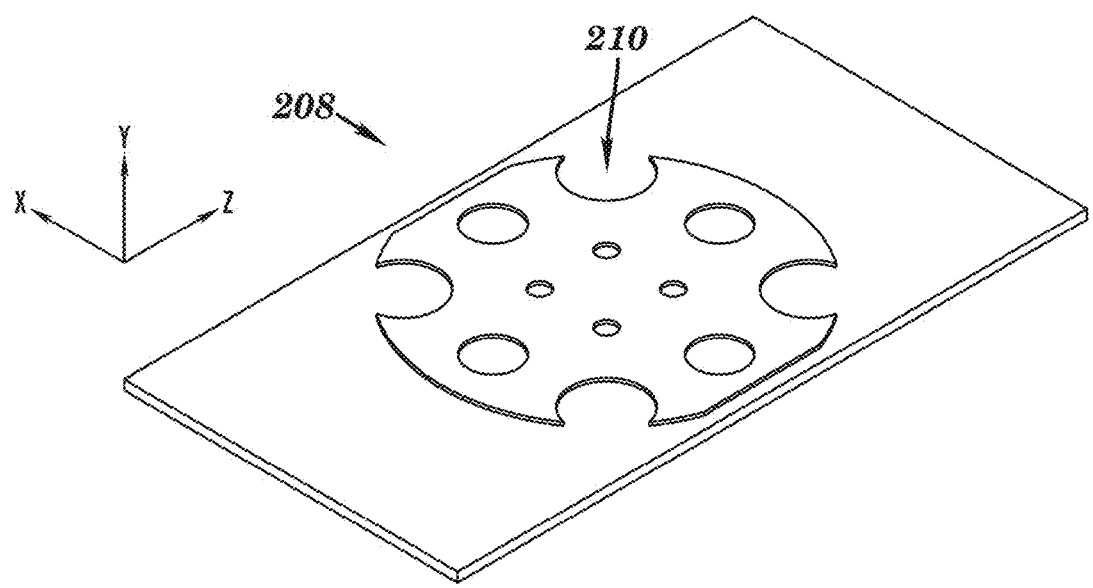
Figure 12B:
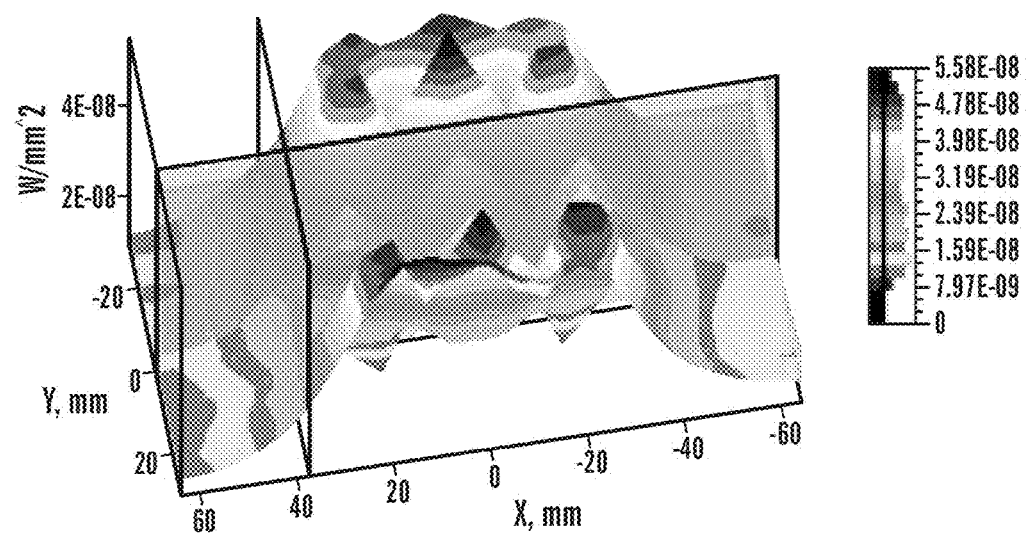

Although the reflecting mirrors 108 in FIGS. 4A and 4B, FIGS. 7A and 7B, and FIGS. 10A and 10B are shown as a cone, it is understood that a reflecting mirror used in conjunction with an illuminator can be any shape. For example, as shown in FIG. 12A, a reflecting mirror 208 can include a complex surface including a plurality of holes 210. The reflecting mirror 208 in this embodiment can comprise a cone shape, a flat circular surface, and/or the like, with the plurality of holes 210. The holes 210 can have varying diameters. For example, as shown in FIG. 12A, the diameter of the holes can increase towards the edge of the reflecting mirror 208. However, it is understood that this is only illustrative and the diameter of the holes can vary according to any predetermined or random pattern. The complex surface of the reflecting mirror 208 can be configured to improve the overall distribution of intensity through the exit surface. In particular, the diameter(s), placement, and number of holes on the complex surface of the reflecting mirror 208 can be selected to improve the uniformity of the intensity. An example of the intensity distribution for the diffusive ultraviolet radiation including this reflecting mirror 208 is illustrated in FIGS. 12B-12D. In this example, the illuminator includes only one ultraviolet radiation source. However, it is understood that the reflecting mirror 208 including the complex surface with the plurality of holes 210 can be incorporated into any illuminator embodiment.

It is understood that the ultraviolet radiation sources can be positioned anywhere within the reflective cavity of the illuminator, including on a surface of the cavity or in the interior of the cavity. To this extent, turning now to FIGS. 13A and 13B, an illustrative illuminator 500 according to an embodiment is shown. In this case, the ultraviolet radiation sources 102 are positioned within the interior of reflective cavity 104 and are configured to direct ultraviolet radiation towards the top surface 106A. In an embodiment, at least 90% of the ultraviolet radiation is directed towards the top surface 106A of the reflective cavity 104. The ultraviolet radiation sources 102 can be mounted on a mounting mesh 510 using any solution. Since at least the top surface 106A of the reflective cavity 104 is at least 70% reflective, the ultraviolet radiation generated by the ultraviolet radiation sources 102 is diffusively reflected off of the top surface 106A and scattered throughout the reflective cavity 104. The mounting mesh 510 can include a plurality of voids 520 to allow the diffused ultraviolet radiation to transmit past the mounting mesh 510 towards the bottom surface 106B to exit the reflective cavity 104. The mounting mesh 510 can also include a material that is highly reflective, such as a highly ultraviolet reflective expanded polytetrafluoroethylene (ePTFE) membrane (e.g., GORE® Diffuse Reflector Product), and/or the like, to improve the overall light intensity distribution and facilitate light scattering and recirculation throughout the reflective cavity 104.

Figure 14A:
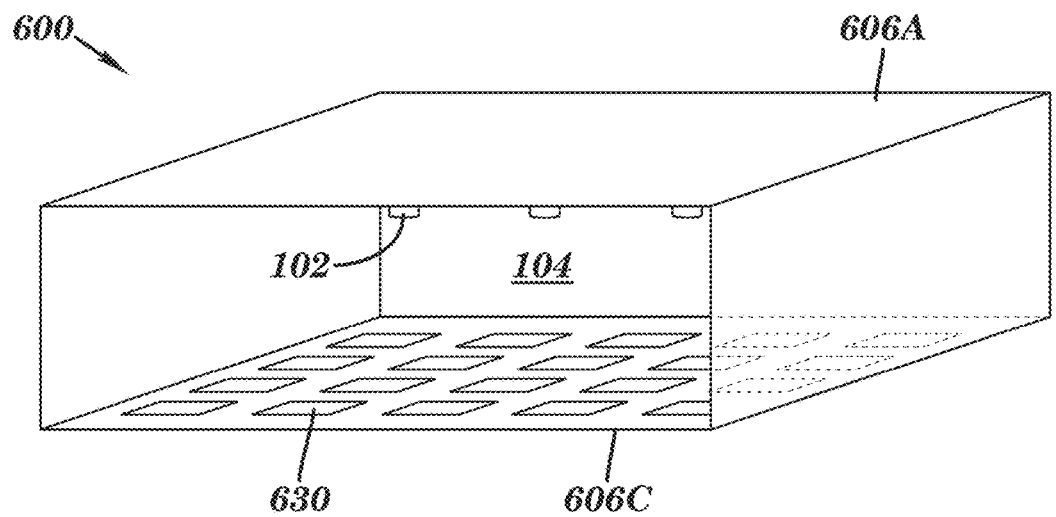
FIGS. 14A and 14B show a cross sectional view and an isometric view, respectively, of an illustrative illuminator according to an embodiment.
Figure 14B:
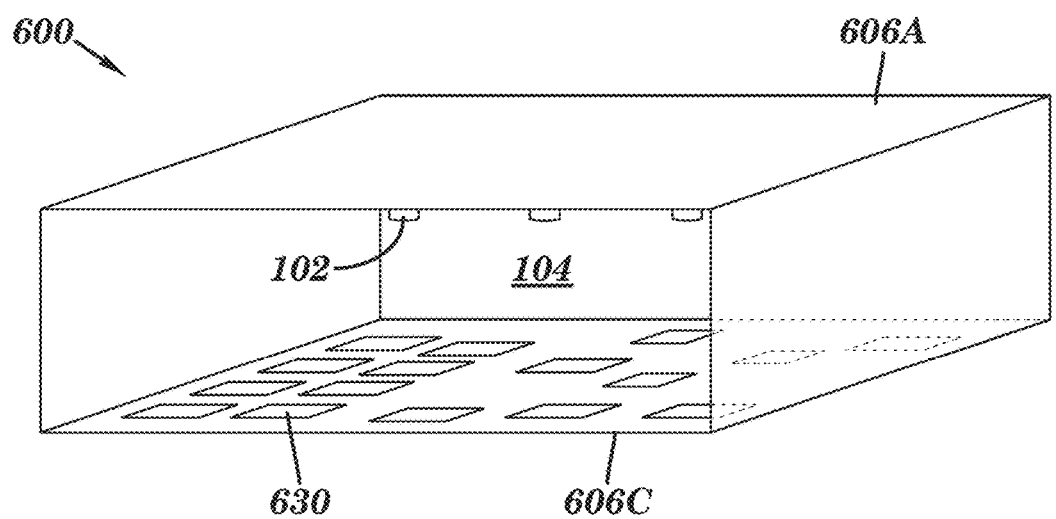

An illuminator can include any combination of one or more of various solutions for diffusing UV radiation. Turning now to FIGS. 14A and 14B, an illustrative illuminator 600 according to an embodiment is shown. While not shown, it is understood that the illuminator 600 can include any combination of one or more features described herein (e.g., reflecting mirrors located below each illuminator). In this embodiment, the ultraviolet radiation sources 102 are mounted on the top surface 606A of the reflective cavity 104. However, the partially transmitting, partially reflecting bottom surface 606C can include a plurality of voids 630, so that the bottom surface 606C is a mesh design. In FIG. 14A, the plurality of voids 630 form an array of rectangular voids. The size, density, and position of each void 630 can be designed to improve radiation uniformity, and can be designed with consideration of the position, size, shape, and power of the ultraviolet radiation sources 102 using any solution. In a specific embodiment, the bottom surface 606C of the reflective cavity 104 can include a Teflon mesh, a patterned metal foil, such as an aluminum foil, and/or the like, which can be produced using a standard stamping technique. The mesh of the bottom surface 606C can also contain micro-patterning, which can be configured to increase light recirculation and recycling. The number, size, and/or arrangement of the plurality of voids 630 can be used to increase the uniformity of the ultraviolet radiation at the bottom (e.g., exit) surface 606C. In FIG. 14B, the plurality of voids 630 can be located in a non-uniform (e.g., random) order and include voids 630 with varying sizes.

Figure 15:
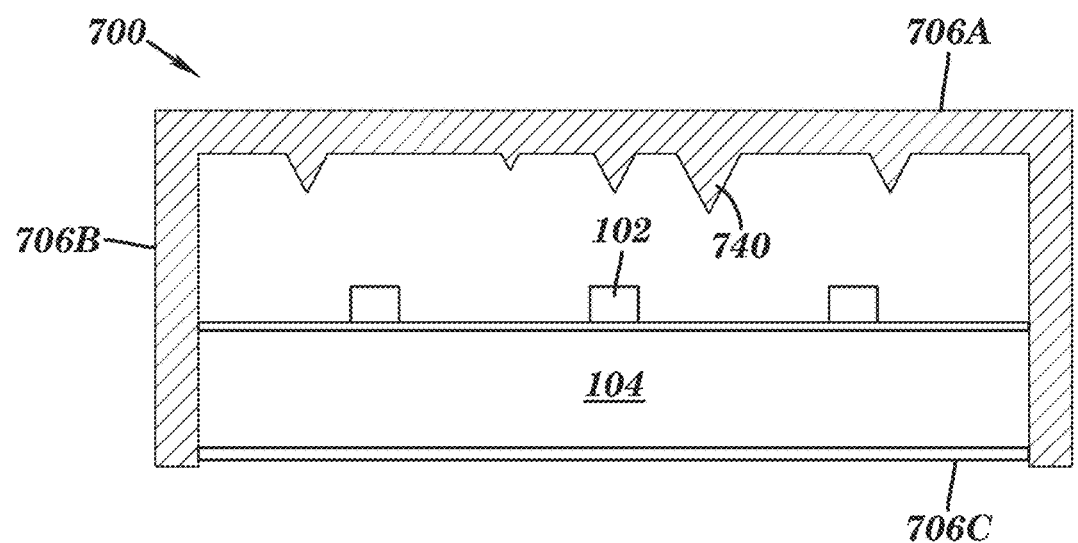
FIG. 15 shows an illustrative illuminator according to an embodiment.

Turning now to FIG. 15, an illustrative illuminator 700 according to an embodiment is shown. In this embodiment, the reflective cavity 104 includes a plurality of diffusive elements 740 along a surface of the reflective cavity 104. For example, as shown in FIG. 15, the plurality of diffusive elements can be located on the top surface 706A of the reflective cavity 104. However, it is understood that the plurality of diffusive elements 740 can be located on any surface of the reflective cavity, such as the side surfaces 706B. Furthermore, in FIG. 15, the plurality of diffusive elements 740 are shown as triangular shaped. Each of the plurality of diffusive elements 740 can include any shape and/or size. The plurality of diffusive elements 740 provides a roughness, patterning, and/or geometrical variations to the corresponding surface of the reflective cavity 104 which can be configured to promote diffusive UV reflection and light recirculation.

Figure 16:
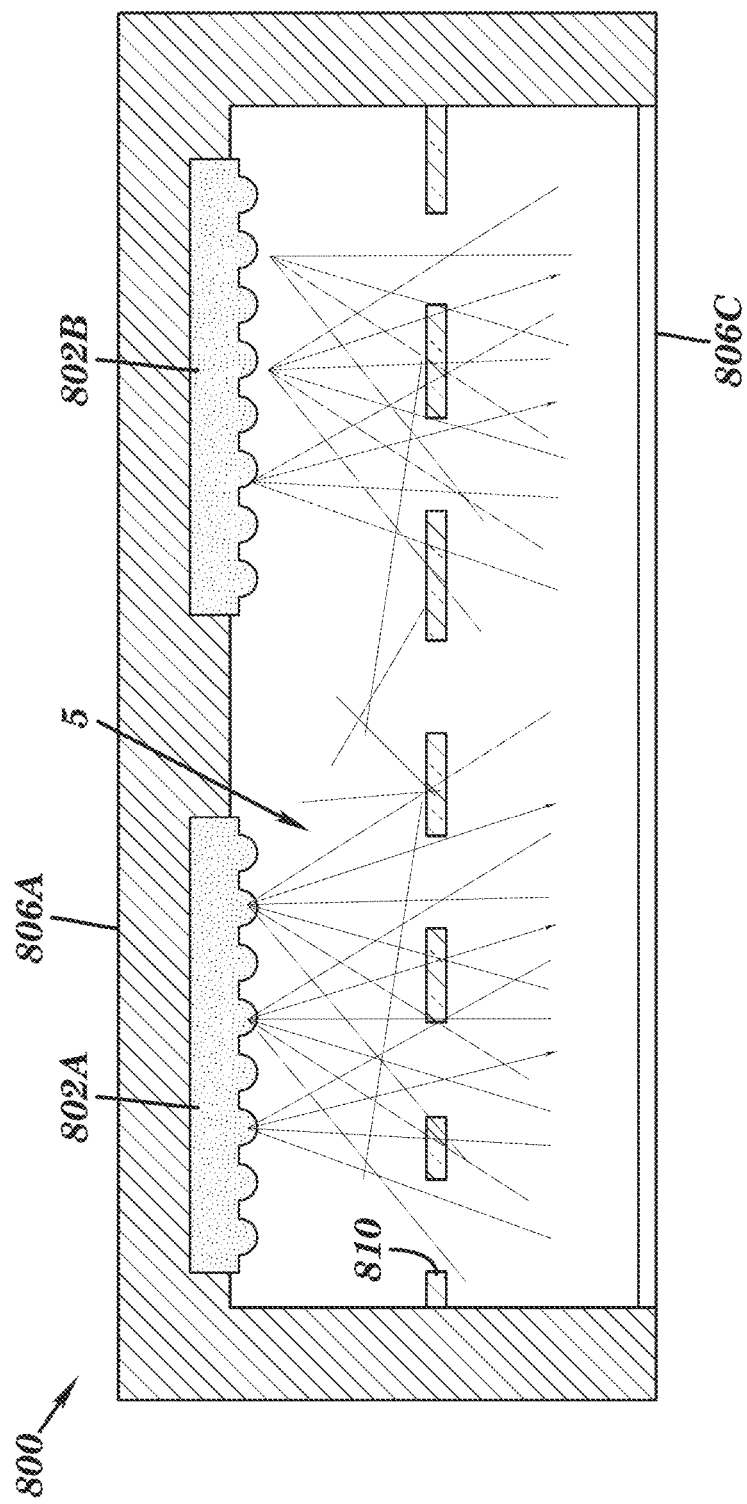
FIG. 16 shows an illustrative illuminator according to an embodiment.

Turning now to FIG. 16, an illustrative illuminator 800 according to an embodiment is shown. In this embodiment, the illuminator 800 can include at least one array of light emitting diodes (LEDs) for providing UV radiation. For example, the illuminator 800 includes a first array of LEDs 802A and a second array of LEDs 802B. The array(s) of LEDs 802A, 802B can help promote uniform emission of the UV radiation over the exit surface (e.g., bottom surface 806C). The illuminator 800 can also include a mesh element

Figure 13A:
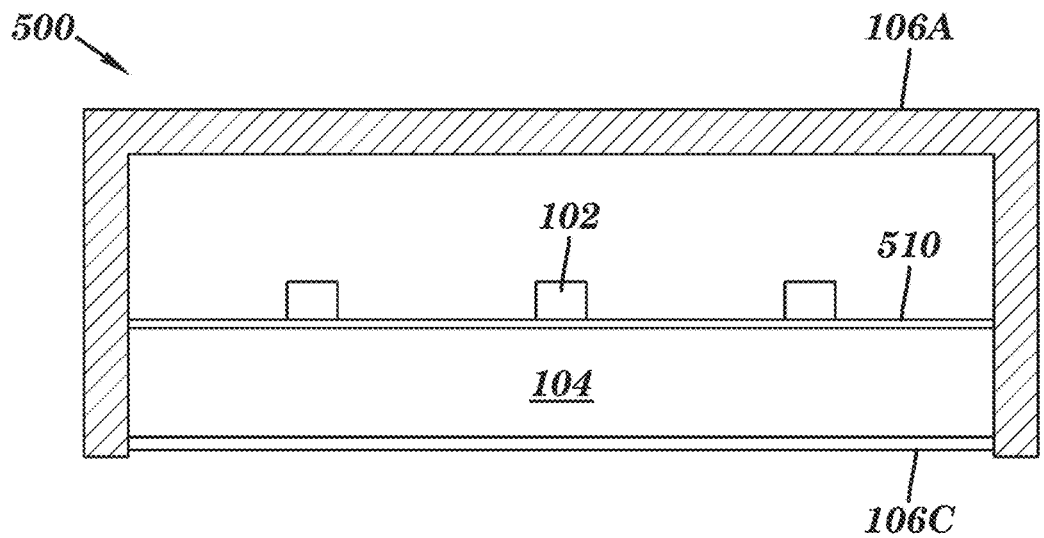
FIGS. 13A and 13B show a cross sectional view and an isometric view, respectively, of an illustrative illuminator according to an embodiment.
Figure 13B:
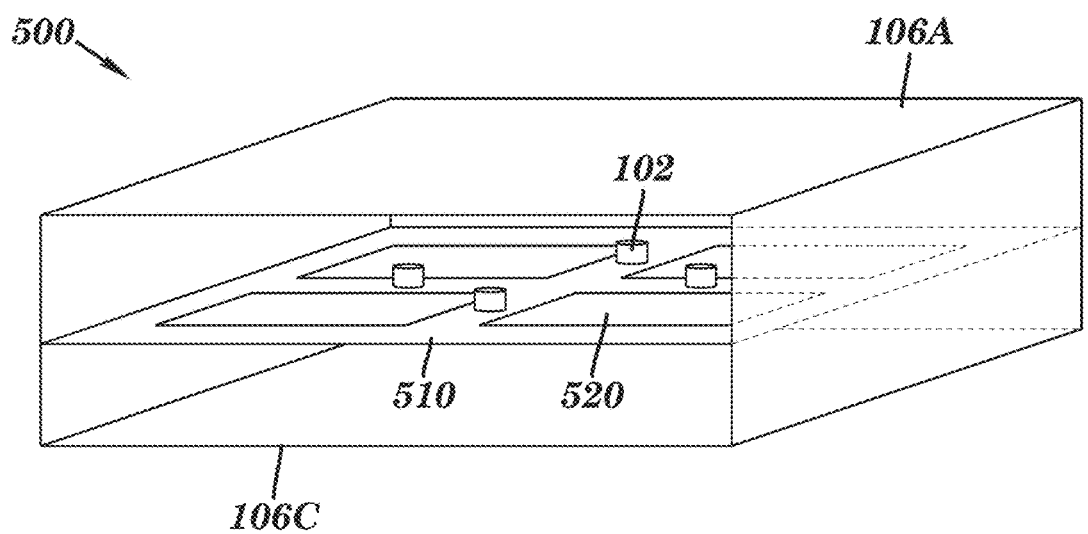

810, which can be configured similar to the mounting mesh 510 shown in FIGS. 13A, 13B. The mesh element 810 can include a material that is diffusively reflective so that the UV radiation is diffusively reflected and light is re-circulated within the reflective cavity 104 before exiting through the bottom surface 806C. The mesh element 810 can comprise a fluoropolymer material, a highly ultraviolet reflective expanded polytetrafluoroethylene (ePTFE) membrane (e.g., GORE® Diffuse Reflector product), and/or the like.

In order to control the transparency and/or reflectivity of a material used within the reflective cavity in an illuminator described herein, any combination of various approaches can be utilized. In an embodiment, a high performance reflective/transparent polymer can be patterned and located within the illuminator. The patterning can be performing using any technique, such as, imprinting, embossing, and/or the like. The patterning can result in voids (e.g., holes) having any of various patterns, so that the material is partially transparent (via the voids) and partially reflective to UV radiation (via its surface). The transparency and reflectivity of the material can be controlled by the size, density, and pattern of the voids produced during the patterning process.

Figure 17:
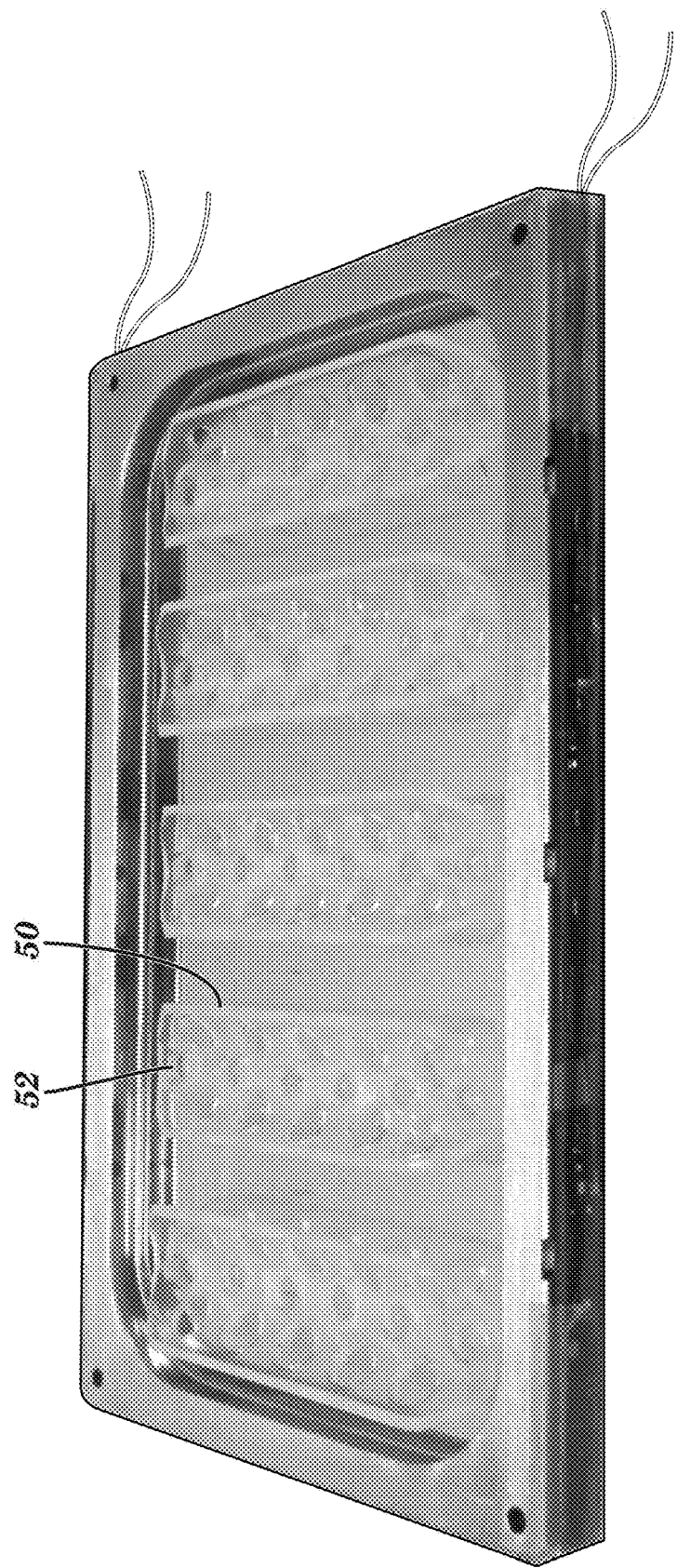
FIG. 17 shows an illustrative patterning on a polymer according to an embodiment.
Figure 18:
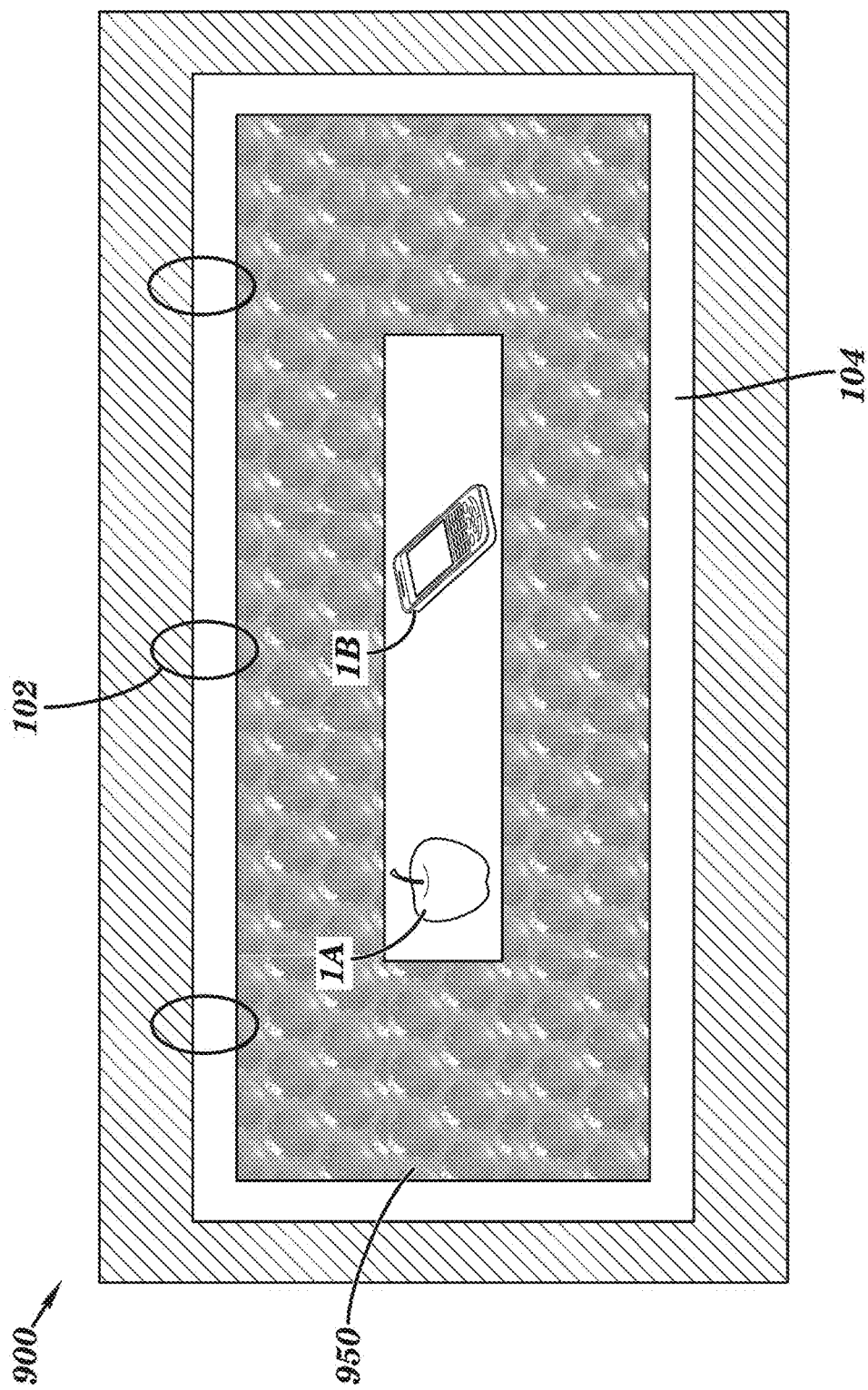
FIG. 18 shows an illustrative enclosure including an illuminator for diffusively reflecting ultraviolet radiation according to an embodiment.
Figure 19:
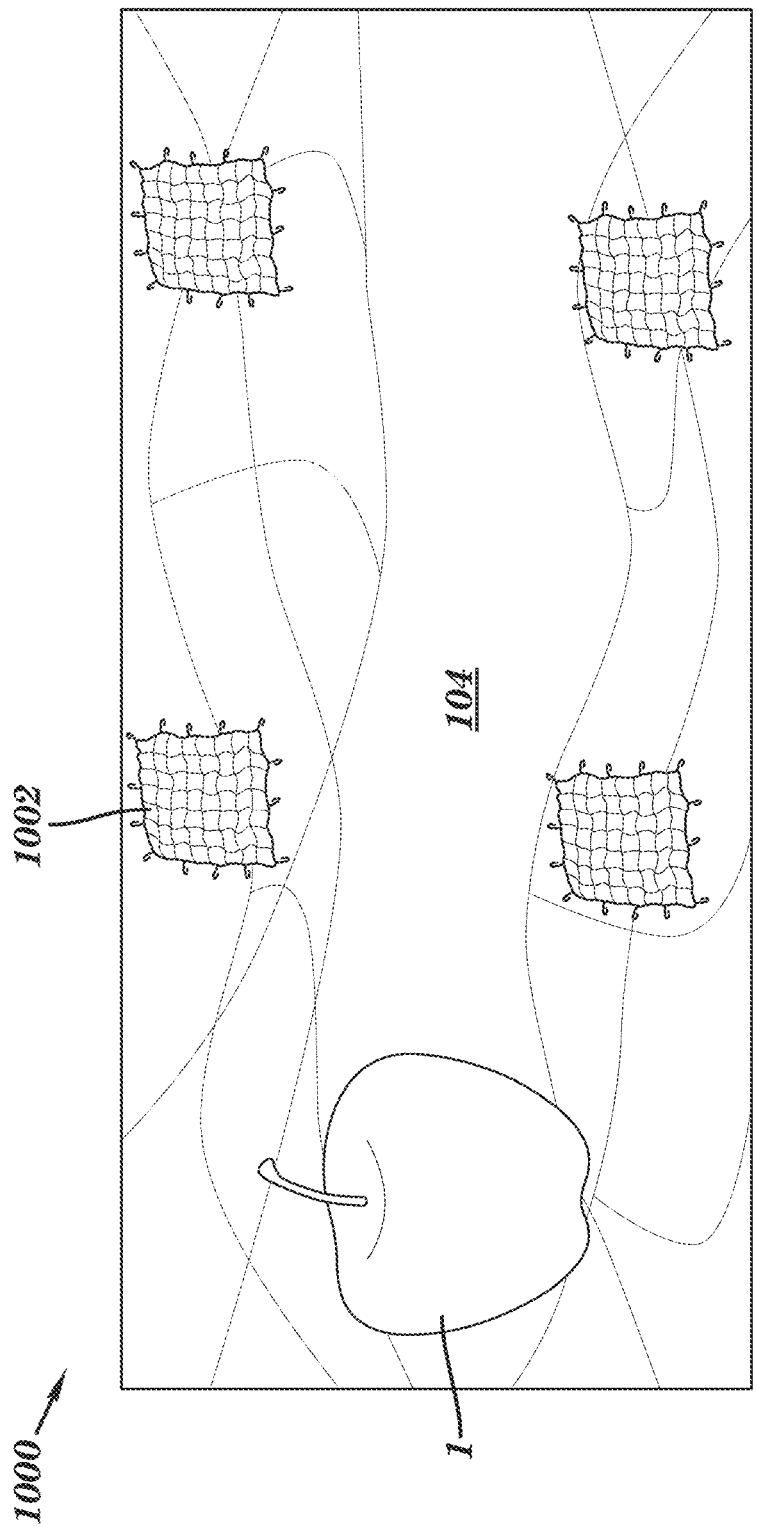
FIG. 19 shows an illustrative enclosure including an illuminator for diffusively reflecting ultraviolet radiation according to an embodiment.
Figure 20A:
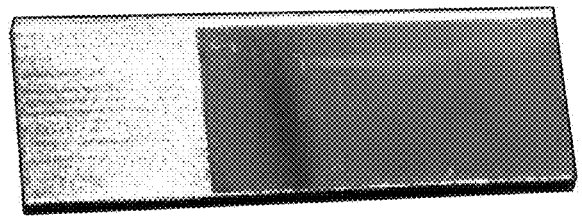
FIGS. 20A and 20B show an example of roughening a reflective surface to achieve diffusive reflectance according to an embodiment.
Figure 20B:
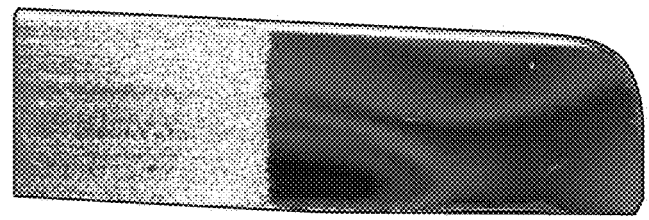

For example, in FIG. 17, a plurality of half-tube strips 50 are shown. The half-tube strips can be formed of a high performance polymer that is patterned to include a plurality of voids 52. The polymer can comprise a material that is partially transparent and partially reflective to ultraviolet radiation. Each half-tube strip 50 can be formed from a tube that is cut in half along the plane that passes through the center axis of the tube. In an embodiment, the plurality of half-tube strips 50 can be connected to a surface of the reflective cavity 104 and used to scatter and circulate the ultraviolet radiation. In another embodiment, as shown in FIG. 18, a transparent polymer 950, such as bubble wrap, can be used to support an item 1A, 1B to be treated (e.g., disinfected) using an illuminator 900 described herein. In FIG. 19, an illuminator 1000 can include a net 1002 that is capable of supporting an item 1 to be disinfected using the illuminator 1000. The net 1002 can contain UV transparent threads formed of a suitable fluoropolymer material that can be used to diffuse and/or waveguide the UV radiation. Roughening, as seen in FIGS. 20A-20B (left sides of material only), can be used to incorporate diffusive scattering into some or all of an interior surface of an illuminator described herein.

Figure 21:
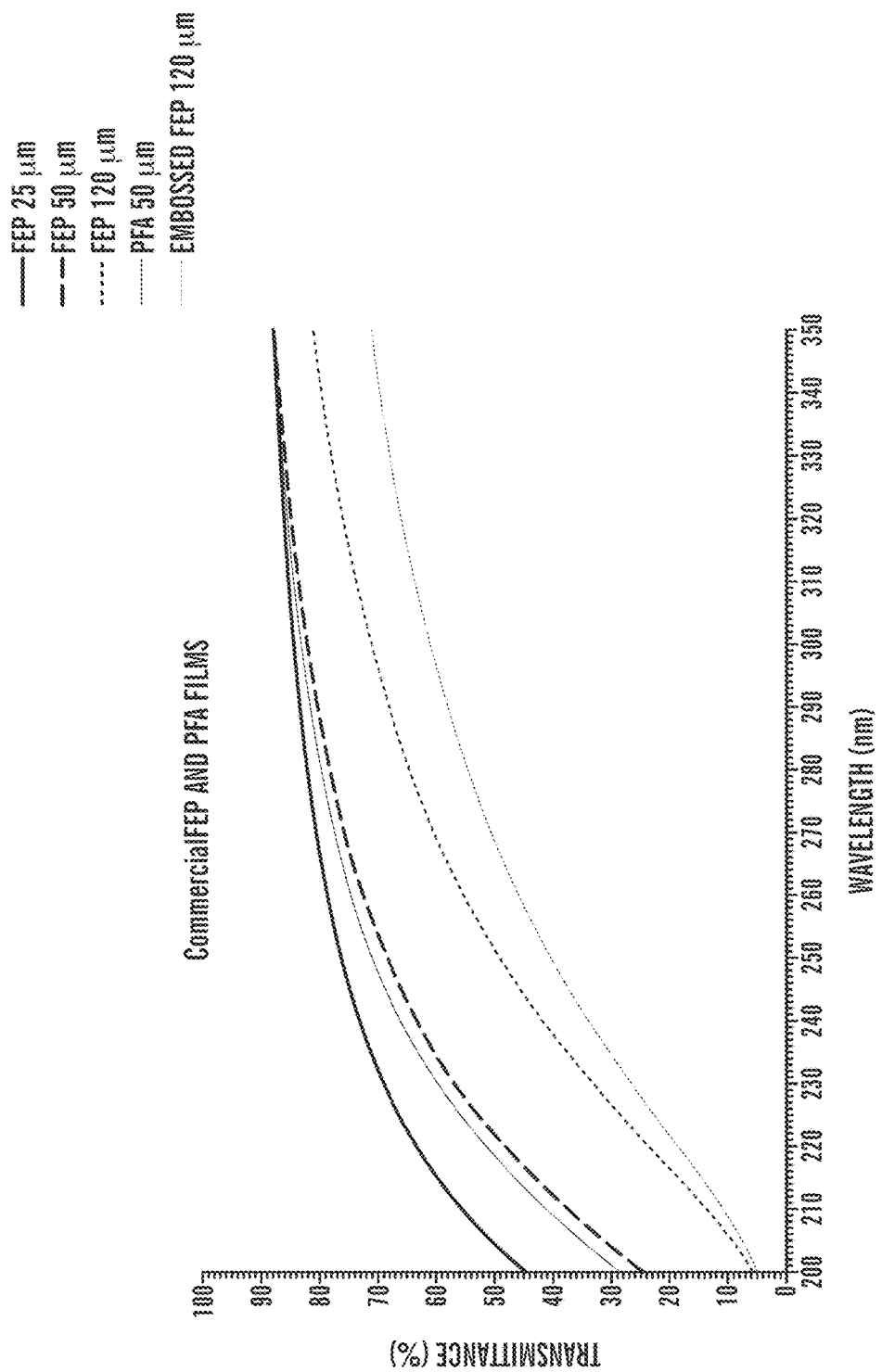
FIG. 21 shows the transmission characteristics for various polymers.
Figure 22B:
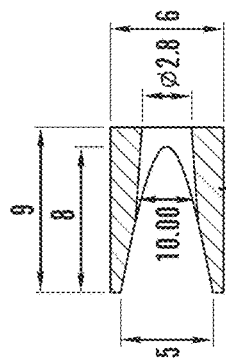
FIGS. 22A-22E show an illustrative parabolic mirror for use in an illuminator according to an embodiment.
Figure 22D:
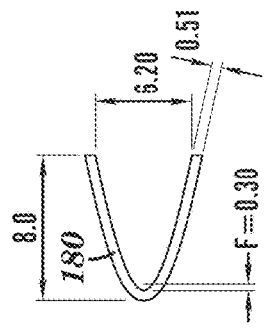
Figure 22A:
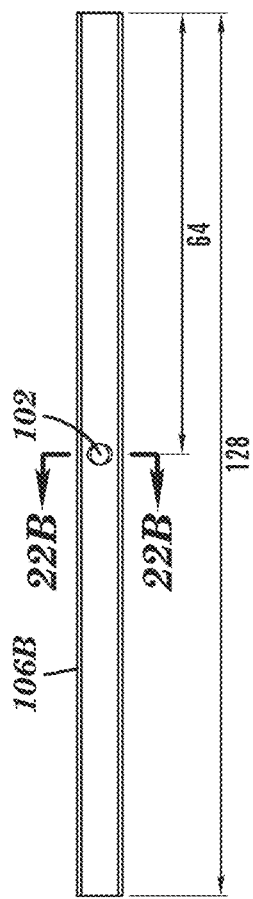
Figure 22C:
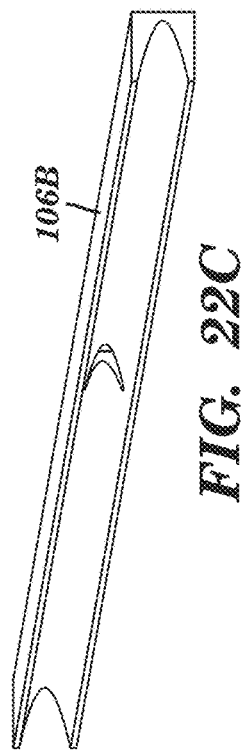
Figure 22E:
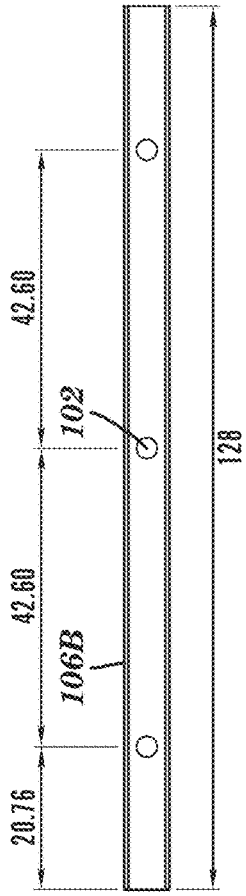

A reflective cavity of an illuminator described herein can include more than one transparent polymer film. For example, polymer films with different index of refractions can be incorporated to form a layered structure, which can result in improved reflective and/or transparent properties of the reflective cavity. In an embodiment, a reflective coating can be applied to a reflective metallic wall on one or more of the surfaces of the reflective cavity within the illuminator. Nano-patterning can result in photonic crystal patterns within such films by altering their optical properties. The high performance polymer can be, for example, polytetrafluoroethylene, such as Teflon, perfluoroalkoxy (PFA), fluorinated ethylene propylene (FEP), and/or the like, and a highly reflective polymer can be a flexible material, such as a highly ultraviolet reflective expanded polytetrafluoroethylene (ePTFE) membrane (e.g., GORE® Diffuse Reflector Material). In FIG. 21, a graph illustrating the transmission characteristics for a plurality of polymers is provided. For FEP films, the transmission can reach 80% at approximately 270 nanometers (nm).

Figure 23:
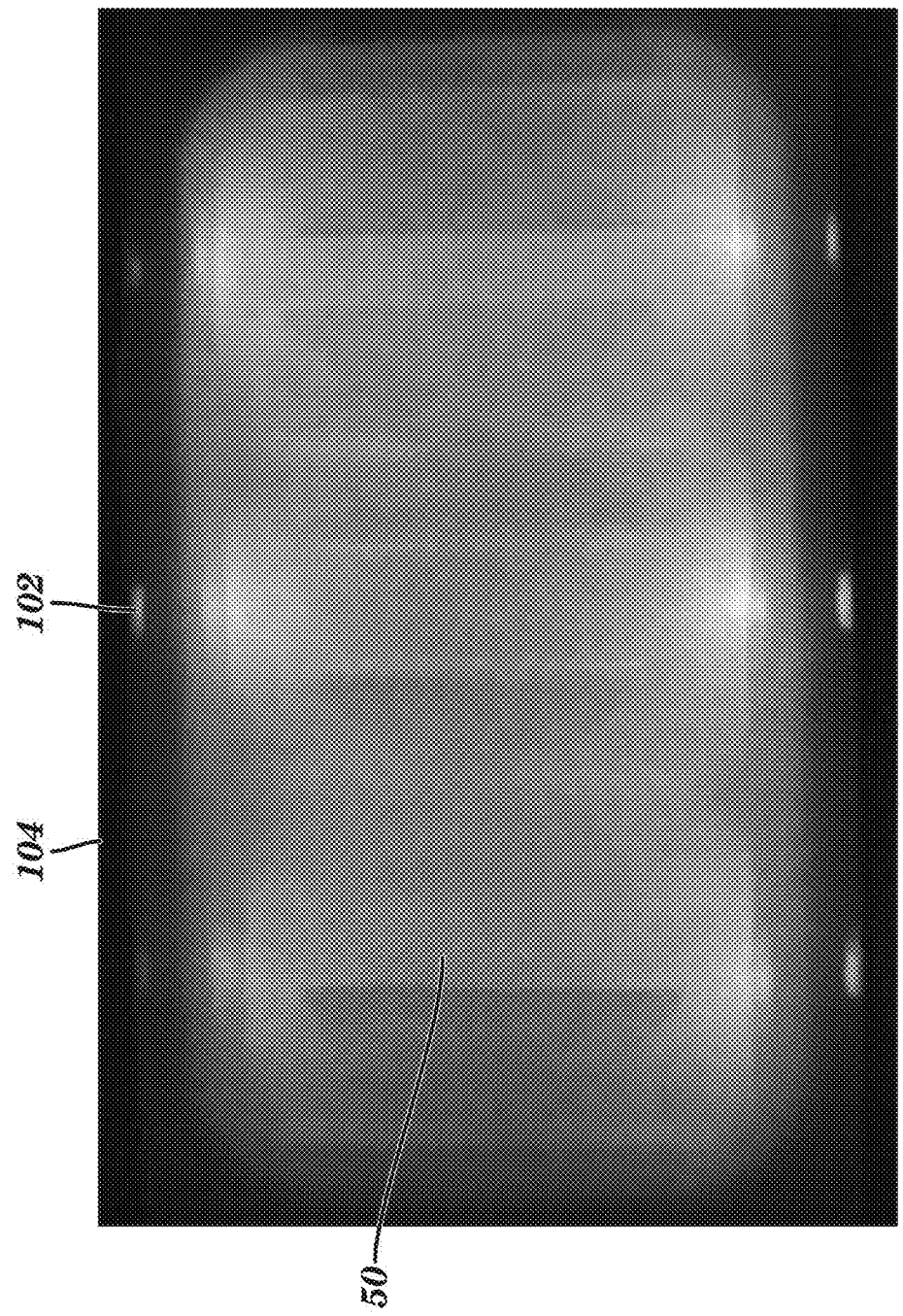
FIG. 23 shows the ultraviolet intensity distribution via photoluminescence of an illuminator with ultraviolet radiation sources positioned on the side.

As described herein, the ultraviolet radiation sources can be located in any combination of various locations within the reflective cavity (e.g., on a top surface of the reflective cavity, within the reflective cavity and supported on a mounting mesh that is along a center axis of the reflective cavity, and/or the like). As shown in FIGS. 22A-22E, at least one ultraviolet radiation source 102 can also be located on a side surface 106B of the reflective cavity. As seen most clearly in the perspective view shown in FIG. 22C, the side surface 106B can include an opening through which light emitted by the radiation source 102 enters the interior of the illuminator. Furthermore, parabolic mirrors can be incorporated within the illuminator, e.g., on the interior of the side surface 106B, to increase the propagation of the UV radiation throughout the chamber. It is understood that the angles and dimensions shown in FIGS. 22A-22E are only illustrative of various angles and dimensions, which can be selected using any solution according to the target size of the item to be disinfected, the target size of the enclosure, the target intensity and/or distribution of the ultraviolet radiation source, and/or the like. FIG. 23 shows an illustrative UV intensity distribution created via photoluminescence within a reflective cavity 104 of an illuminator including UV radiation sources 102 located at the side surfaces according to an embodiment. In this embodiment, half-tube strips 50 (FIG. 17) are included within the reflective cavity 104 to further recycle and diffusive UV radiation.

A diffusive UV illuminator described herein can be incorporated into a disinfection device, which can be configured to disinfect any type of item. For example, the illuminator can be used to disinfect an electronic gadget, a food item, and/or the like. An illuminator described herein can be incorporated with an existing enclosure, and also be configured to disinfect the enclosure (e.g., a cell phone case, a refrigeration system, and/or the like) and/or the items stored in the enclosure. The enclosure can include a rotatable holder for items stored therein, so that the items are thoroughly exposed to the ultraviolet radiation.

FIG. 24 shows a schematic of an UV disinfection enclosure 60 for disinfecting electronic gadgets that includes an UV illuminator 62. The UV illuminator 62 can be located on the top, and can be hingedly connected to enable a contaminated surface of the electronic gadget to be disinfected by radiating diffusive UV radiation onto the surface. Furthermore, it is understood that the UV disinfection enclosure 60 can include two or more UV illuminators 62, each of which is configured to emit diffusive UV radiation directed at a unique surface or a unique portion of a surface of an object to the disinfected. Regardless, the ultraviolet radiation can be turned off when the top cover is open and the interior (e.g., the face of the electronic gadget) is exposed. The enclosure 60 can also include a mechanism for ejecting the item (e.g., an electronic gadget) when the cover is open. Use of diffusive UV radiation can provide an effective disinfection of an item even with a relatively low power of UV radiation. For example, turning now to FIGS. 25A and 25B, in an embodiment, a substantial reduction of *e. coli* colonies is achieved by disinfecting for approximately 40 minutes using a weak UV radiation of about 1 microwatt per centimeter squared.

Figure 26:
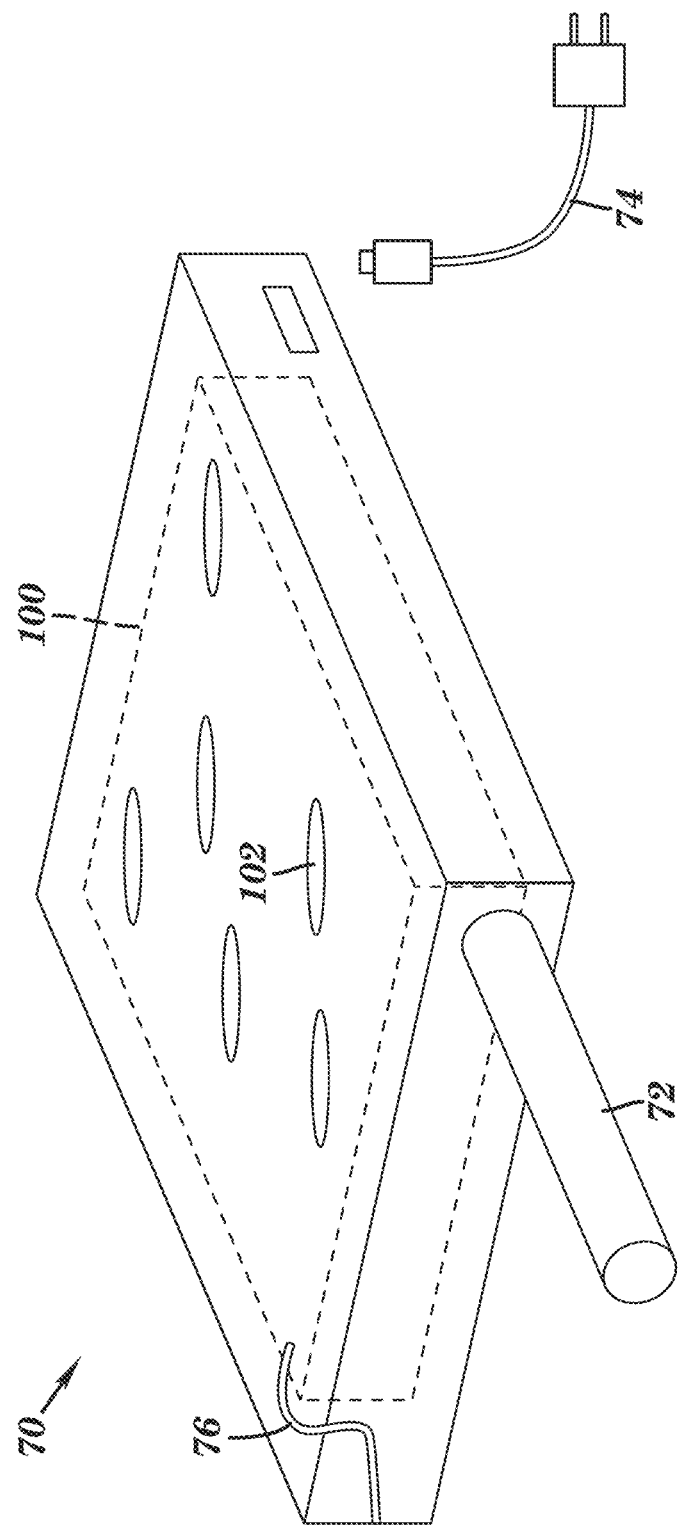
FIG. 26 shows an illustrative enclosure including a diffusive illuminator according to an embodiment.

Turning now to FIG. 26, a UV disinfection enclosure 70 including an illuminator 100 according to an embodiment is shown. For example, the illuminator 100 can be configured similar to the illuminator shown in FIG. 3. However, it is understood that this is only illustrative, and it is understood that the enclosure 70 can include an illuminator according to any of the embodiments discussed herein. The enclosure 70 can include an antenna 72 for improving reception of a signal to an electronic gadget that will be disinfected within the enclosure 70. The antenna 72 can be used for various purposes, such as, to amplify a signal to the electronic gadget, improve reception of a radio or microwave signal, and/or the like. In this manner, the electronic gadget located therein can continue to operate while being disinfected. The enclosure 70 can also include a power cable and/or a data cable 74 that can be used to connect to and provide power to the electronic gadget that will be disinfected by the enclosure 70. The enclosure 70 can also include a cable 76 that is used to connect a component associated with and/or external to the enclosure 70 to the electronic gadget. For example, such a connection can be used for data exchange between a computing device of the enclosure 70 and the electronic gadget, supplying power to and/or recharging the electronic gadget, and/or the like.

Figure 27:
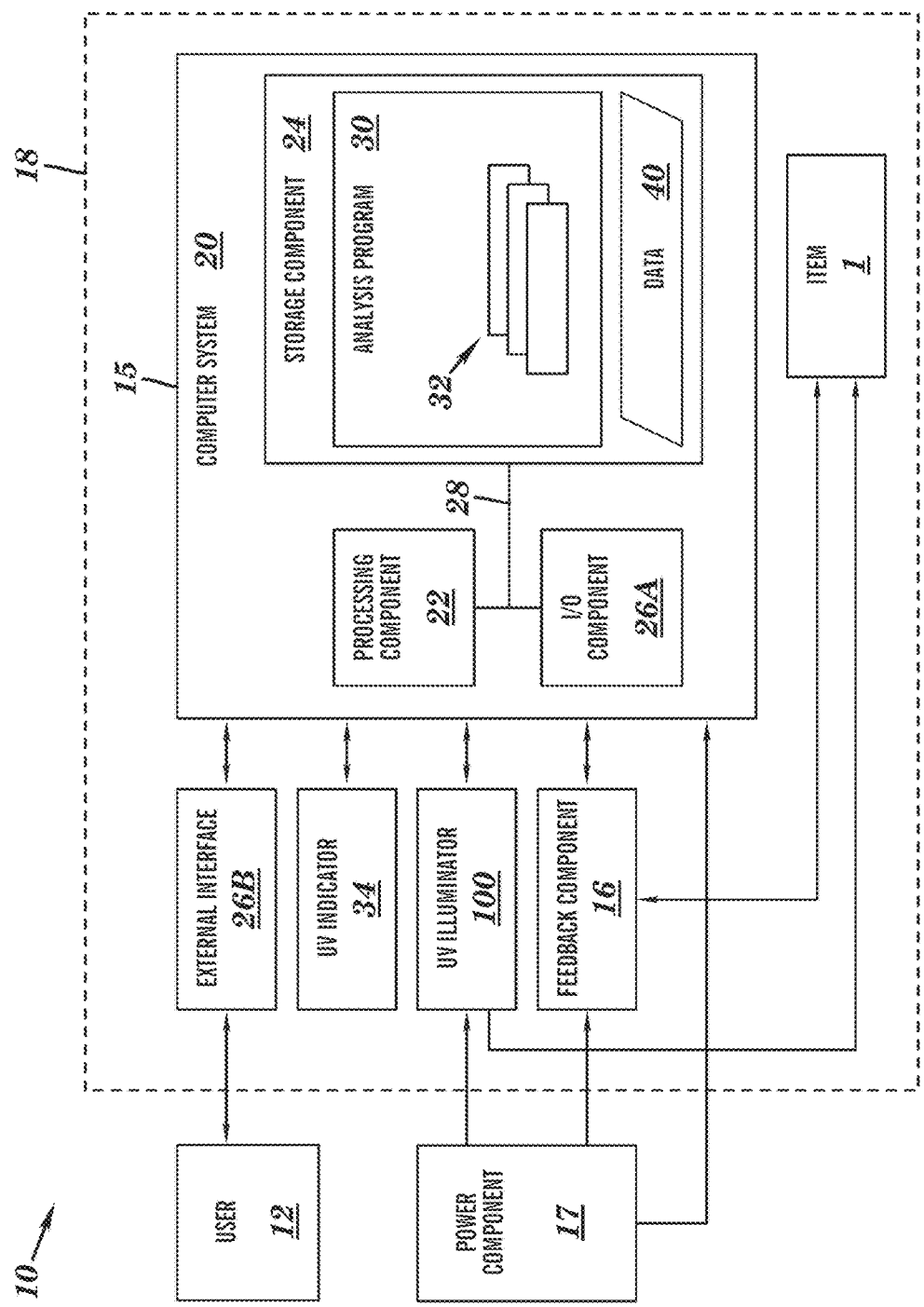
FIG. 27 shows an illustrative ultraviolet radiation system including a diffusive illuminator according to an embodiment.

Turning now to FIG. 27, an illustrative ultraviolet radiation system 10 according to an embodiment is shown. In this case, the system 10 includes a monitoring and/or control system 15, which can be incorporated in a disinfection enclosure 18 and/or located apart from the disinfection enclosure 18. Regardless, the monitoring and/or control system 15 can be implemented as a computer system 20 including an analysis program 30, which makes the computer system 20 operable to manage a diffusive ultraviolet radiation illuminator 100 by performing a process described herein. In particular, the analysis program 30 can enable the computer system 20 to operate the diffusive ultraviolet radiation illuminator 100 to generate and direct ultraviolet radiation toward the item 1 to be disinfected and process data corresponding to one or more attributes regarding the item 1, which is acquired by a feedback component 16, and/or an ultraviolet radiation history stored as data 40.

While a single diffusive ultraviolet radiation illuminator 100 is shown, it is understood that the enclosure 18 can include any number of diffusive ultraviolet radiation illuminators 100, the operation of which the computer system 20 can collectively and/or separately manage using a process described herein. Further, a single diffusive ultraviolet radiation illuminator 100 can include any number of ultraviolet radiation sources. In any case, it is understood that the computer system 20 can individually control each ultraviolet radiation source within the diffusive ultraviolet radiation illuminator 100, each diffusive ultraviolet radiation source, and/or control two or more of the ultraviolet radiation sources as a group.

In an embodiment, during an initial period of operation (e.g., after an item 1 is placed within or attached to the enclosure 18, and/or the like), the computer system 20 can acquire data from the feedback component 16 regarding one or more attributes of the item 1 and generate data 40 for further processing. The data 40 can include a presence of biological activity (e.g., microorganisms, viruses, bacteria, and/or the like) on a surface of the item 1, a usage history of the item 1 (e.g., timestamps for the removal of and relocation of the item 1 in the enclosure 18), a frequency of usage of the item 1, a disinfection schedule history for the item 1, and/or the like. The feedback component 16 can utilize detectors of UV, visible, and/or infrared radiation that can be used to analyze the radiation from the object to determine the data 40 using any solution. The computer system 20 can use the data 40 to control one or more aspects of the ultraviolet radiation generated by the ultraviolet radiation source(s) 14 in order to disinfect the item 1.

Furthermore, one or more aspects of the operation of the ultraviolet radiation source within the illuminator 100 can be controlled by a user 12 via an external interface component 26B. The external interface component 26B can be located on an exterior of the enclosure 18 and allow the user 12 to choose when to turn on the ultraviolet radiation source (e.g., the illuminator 100). However, it is understood that the sensor and/or switch can still determine the presence of the item 1 within the enclosure 18 and that enclosure 18 is closed in order to generate ultraviolet radiation to avoid harming the user 12. The external interface component 26B can include a touch screen that shows control dials for adjusting an intensity, scheduling, and other operational properties of the ultraviolet radiation source(s). In an embodiment, the external interface component 26B can include a keyboard, a plurality of buttons, a joystick-like control mechanism, and/or the like, to control the ultraviolet radiation source(s).

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 12 to interact with the computer system 20 and/or one or more communications devices to enable a system user 12 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 12 to interact with the analysis program 30. Furthermore, the analysis program 30 can manage (e.g., store, retrieve, create, manipulate, organize, present, etc.) the data, such as data 40, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 15 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 15, such as one which can be implemented without any type of computing device.

Regardless, when the computer system 20 includes multiple computing devices, the computing devices can communicate over any type of communications link. Furthermore, while performing a process described herein, the computer system 20 can communicate with one or more other computer systems, such as the user 12, using any type of communications link. In either case, the communications link can comprise any combination of various types of wired and/or wireless links; comprise any combination of one or more types of networks; and/or utilize any combination of various types of transmission techniques and protocols, such as Bluetooth.

The system 10 also can include an ultraviolet radiation indicator 34 (e.g., an LED), which can be operated by the computer system 20 to indicate when ultraviolet radiation is being generated and directed at the item 1 within the enclosure 18. The ultraviolet radiation indicator 34 can include one or more LEDs for emitting a visual light for the user 12.

The computer system 20 is configured to control the ultraviolet radiation source within the UV illuminator 100 to direct diffusive ultraviolet radiation at the item 1. The feedback component 16 is configured to acquire data used to monitor a plurality of attributes regarding the item 1 over a period of time. The feedback component 16 can include a plurality of sensing devices, each of which can acquire data used by the computer system 20 to monitor the set of attributes.

It is understood that the plurality of attributes for the item 1 can include any combination of one or more of: a frequency of the usage of the item 1, a presence of biological activity on the item 1, a usage of the item, a disinfection schedule history for the item 1, and/or the like. In the case of determining usage details for the item 1, a sensing device (feedback component 16) can include a sensor and/or a switch to sense that an item 1 is physically contained within the enclosure 18. Alternatively, the sensor and/or switch can sense that the item 1 is not located within the enclosure 18 and assume that the item 1 is being used.

In the case of determining a presence of biological activity on the item 1, the feedback component 16 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the feedback component 16 can determine information on the variation of the biological activity over time, such as a growth rate, a rate with which an area including the biological activity is spreading, and/or the like. In an embodiment, a set of biological activity dynamics are related to various attributes of bacteria and/or virus activity on the item 1, including, for example, the presence of detectable bacteria and/or virus activity, measured bacteria and/or virus population/concentration time dynamics, growth phase, and/or the like.

In an embodiment, to determine the presence of biological activity on the item 1, the feedback component 16 includes at least one of: a visual camera or a chemical sensor. The visual camera can acquire visual data (e.g., visual, electronic, and/or the like) used to monitor the item 1, while the chemical sensor can acquire chemical data (e.g., chemical, electronic, and/or the like) used to monitor the item 1. For example, when the computer system 20 is operating the diffusive UV illuminator 100, the feedback component 16 monitoring the item 1 may be operated to detect the presence of microorganisms. In a specific embodiment, the visual camera comprises a fluorescent optical camera that can detect bacteria and/or viruses that become fluorescent under ultraviolet radiation. However, it is understood that a visual camera and a chemical sensor are only illustrative of various types of sensors that can be implemented. For example, the feedback component 16 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the item 1.

The computer system 20 can be configured to control and adjust a direction, an intensity, a pattern, and/or a spectral power (e.g., wavelength) of the at least one ultraviolet radiation source within the illuminator 100, based on the feedback component 16. The computer system 20 can control and adjust each property of the ultraviolet radiation source independently. For example, the computer system 20 can adjust the intensity, time duration, and/or time scheduling (e.g., including duration (e.g., exposure/illumination time)), duty cycle, time between exposures/illuminations, and/or the like) of the ultraviolet radiation source for a given wavelength. In a further embodiment, the feedback component 16 can include a sensor configured to evaluate an operating condition of the UV illuminator 100. To this extent, the UV illuminator 100 can include one or more surfaces (e.g., a surface of a reflector 108 (FIG. 4B), an interior surface 106A, 106C (FIG. 4B), and/or the like), which is at least partially coated with a photoluminescent pigment. In this case, during and/or after operation of the UV illuminator 100, the feedback component 16 can sense (e.g., with a visual camera) whether the photoluminescent pigment is emitting visible light. In addition, the photoluminescent pigment can configured to be visible external to the UV illuminator 100, in which case the pigment can provide an indication to the user 12 that the UV sources are operating. The computer system 20 can correlate amount of visible light being emitted by the pigment with an operating condition of one or more of the ultraviolet sources in the UV illuminator 100. Each of the properties of the ultraviolet radiation source can be adjustable and controlled by the computer system 20 according to data provided by the feedback component 16.

For example, the computer system 20 can be configured to adjust the direction of the ultraviolet radiation according to a location of the biological activity detected on the item 1 by the feedback component 16 using any solution. The computer system 20 can be configured to utilize a target timing, intensity, and/or spectral power of the ultraviolet radiation according to a type of biological activity. That is, the sensing devices 39 can sense locations of higher levels of biological activity on the item 1, and the ultraviolet radiation source 14 can be configured by the computer system 20 to direct higher doses (by increasing intensity or exposure) of ultraviolet radiation at the locations with higher levels of biological activity (e.g., non-uniform ultraviolet radiation).

The feedback component 16 can also sense (via sensor and/or switch) that the item 1 is physically contained within the enclosure 18. In response to detection of the item 1 being located within the enclosure 18, the computer system 20 can be configured to automatically turn on the ultraviolet radiation. In one embodiment, the computer system 20 can be configured to set a periodic or an aperiodic schedule for the ultraviolet radiation when the item 1 is within the enclosure 18. This (periodic or aperiodic) schedule can be interrupted when the feedback component 16 senses that the item 1 is removed from the enclosure 18 and the computer system 20 can be configured to turn off the ultraviolet radiation. In this case, the schedule (periodic or aperiodic) can be resumed once the feedback component 16 senses the item 1 within the enclosure 18 again. The feedback component 16 can also sense that the enclosure 18 is open. In this example, the computer system 20 can be configured to turn off the ultraviolet radiation.

It is understood that the system 10 may include a power component 17 that is implemented separately from the item 1 to supply power to one or more of the various components of system 10, such as UV illuminator 100, feedback component 16, computer system 20, and/or the like. For example, the item 1 may comprise a power source that is insufficient to operate the various devices of system 10 in addition to maintaining sufficient power to continue one or more aspects of the operation of the item 1. Regardless, the power component 17 can be utilized to operate system 10. The power component 17 can comprise any source of power including, but not limited to, a battery set, a solar cell, and/or the like. For example, the power component 17 can include any of various types of rechargeable batteries (e.g., lithium ion, nickel-cadmium, and/or the like). The power component 17 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a Universal Serial Bus (USB) connection.

In an embodiment, the computer system 20 can implement multiple modes of operation depending on the source of power and/or an amount of power remaining. In particular, when a power component 17 of limited capacity is being utilized, one or more functions of system 10 can be disabled and/or reduced to lengthen an operating time for system 10. In another embodiment, a data-electrical link can be made between the item 1 and the enclosure 18 for data and/or power exchange between the item 1 and the computer system 20. For example, the item 1 and the enclosure 18 can be charged simultaneously via this data-electrical link. Additionally, the computer system 20 can provide data (via wireless and/or wired means) regarding the disinfection of the item 1 to the item 1, which can be presented to the user 12 (e.g., via an app installed on the item 1). In another embodiment, the power component 17 can comprise an electrical cord for charging the enclosure 18 via a household outlet.

While shown and described herein as a method and system for disinfecting an item using diffusive UV radiation, it is understood that aspects of the invention further provide various alternative embodiments. For example, in one embodiment, the invention provides a computer program fixed in at least one computer-readable medium, which when executed, enables a computer system to disinfect the item using a process described herein. To this extent, the computer-readable medium includes program code, such as the analysis program 30 (FIG. 27), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the analysis program 30 (FIG. 27), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting an item. In this case, the generating can include configuring a computer system, such as the computer system 20 (FIG. 27), to implement a method of disinfecting the item as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    an illuminator including:
        a reflective cavity comprising a plurality of surfaces, wherein at least one of the plurality of surfaces is formed of a first material configured to reflect at least 70% of ultraviolet radiation, wherein the first material is patterned to include a plurality of diffusive elements, and wherein at least one of the plurality of surfaces is formed of a second material configured to transmit at least 30% of the ultraviolet radiation through the second material and out of the reflective cavity and reflect at least 10% of the ultraviolet radiation;
        a plurality of ultraviolet radiation sources located within the reflective cavity; and
        a set of optical elements located within the reflective cavity and configured to distribute the ultraviolet radiation within the cavity before the ultraviolet radiation exits the reflective cavity through the second material, wherein each optical element is located a distance away from an ultraviolet radiation source, and wherein the distance is approximately equal to a diameter of the corresponding ultraviolet radiation source and is configured to increase uniformity of the ultraviolet radiation exiting the reflective cavity;
    a feedback component including a sensor configured to acquire fluorescence data corresponding to fluorescent visible radiation emitted from a surface radiated by the illuminator; and
    a computer system for operating the plurality of ultraviolet radiation sources based on the fluorescence data.

2. The system of claim 1, wherein the first material is configured to diffusively reflect the ultraviolet radiation.

3. The system of claim 1, wherein the plurality of ultraviolet radiation sources are mounted on a mounting mesh located within the reflective cavity.

4. The system of claim 3, wherein the mounting mesh is configured to reflect at least 70% of the ultraviolet radiation into the reflective cavity.

5. The system of claim 4, wherein the mounting mesh diffusively reflects the radiation.

6. The system of claim 3, wherein the mounting mesh is configured to transmit at least 70% of the ultraviolet radiation into the reflective cavity.

7. The system of claim 1, wherein the second material comprises fluoropolymer.

8. The system of claim 1, wherein the second material includes patterning forming a plurality of openings.

9. The system of claim 8, wherein the plurality of openings have a pattern configured to improve a uniformity of an intensity of the ultraviolet radiation.

10. A system comprising:
    an enclosure configured to contain an object for disinfection;
    an illuminator located within the enclosure, the illuminator comprising
        a reflective cavity comprising a plurality of surfaces, wherein at least one of the plurality of surfaces is formed of a first material configured to diffusively reflect at least 70% of ultraviolet radiation, wherein the first material is patterned to include a plurality of diffusive elements, and wherein at least one of the plurality of surfaces is formed of a second material configured to transmit at least 30% of the ultraviolet radiation through the second material and out of the reflective cavity and reflect at least 10% of the ultraviolet radiation;
        at least one ultraviolet radiation source configured to generate the ultraviolet radiation directed into the reflective cavity; and
        a set of optical elements located within the reflective cavity and configured to distribute the ultraviolet radiation within the cavity before the ultraviolet radiation exits the reflective cavity through the second material, wherein each optical element is located a distance away from an ultraviolet radiation source, and wherein the distance is approximately equal to of a diameter of the corresponding ultraviolet radiation source and is configured to increase uniformity of the ultraviolet radiation exiting the reflective cavity;
    a feedback component including a sensor configured to acquire fluorescence data corresponding to fluorescent visible radiation emitted from a surface of the object radiated by the illuminator; and
    a computer system for operating the at least one ultraviolet radiation source based on the fluorescence data.

11. The system of claim 10, wherein the set of optical elements includes a mesh located within the reflective cavity.

12. The system of claim 10, wherein the sensor includes a fluorescent optical camera.

13. The system of claim 10, wherein the fluorescence data includes data regarding a location of biological activity on the surface.

14. The system of claim 10, wherein the at least one ultraviolet radiation source includes a plurality of ultraviolet radiation sources independently operable by the computer system.

15. The system of claim 10, wherein the feedback component further includes a sensor configured to acquire operating data for the at least one ultraviolet radiation source.

16. An illuminator comprising:
    at least one ultraviolet radiation source configured to generate ultraviolet radiation;
    a reflective cavity comprising a plurality of surfaces, wherein the ultraviolet radiation is directed within the reflective cavity, wherein at least one of the plurality of surfaces is formed of a first material configured to diffusively reflect at least 70% of the ultraviolet radiation, and the diffusively reflected ultraviolet radiation is less than approximately 10% different from a diffusive Lambertian reflectivity for an angle of reflectance, wherein the first material is patterned to include a plurality of diffusive elements, and wherein at least one of the plurality of surfaces is formed of a second material configured to transmit at least 30% of the ultraviolet radiation through the second material and out of the reflective cavity;
    a set of optical elements located within the reflective cavity and configured to distribute the ultraviolet radiation within the reflective cavity before the ultraviolet radiation exits the reflective cavity through the second material, wherein each optical element is located a distance away from an ultraviolet radiation source configured to increase uniformity of the ultraviolet radiation exiting the reflective cavity, and wherein the distance is approximately equal to a diameter of the corresponding ultraviolet radiation source and is configured to increase uniformity of the ultraviolet radiation exiting the reflective cavity;

a feedback component including a sensor configured to acquire operating data for the at least one ultraviolet radiation source; and a computer system for operating the at least one ultraviolet radiation source based on the operating data.

17. The illuminator of claim 16, wherein the feedback component further includes a sensor configured to acquire fluorescence data corresponding to fluorescent visible radiation emitted from a surface radiated by the illuminator, and wherein the computer system adjusts operating the at least one ultraviolet radiation source based on the fluorescence data.

18. The illuminator of claim 16, wherein the at least one ultraviolet radiation source includes a plurality of ultraviolet radiation sources independently operable by the computer system.

19. The illuminator of claim 16, wherein the second material includes patterning forming a plurality of openings having a pattern configured to improve a uniformity of an intensity of the ultraviolet radiation.

20. The illuminator of claim 16, further comprising a partially transparent, partially reflective mesh located within the reflective cavity configured to diffusively reflect the ultraviolet radiation.

* * * * *